United States Patent [19]
Moullier et al.

[11] Patent Number: 5,906,817
[45] Date of Patent: May 25, 1999

[54] BIOCOMPATIBLE IMPLANT FOR THE EXPRESSION AND IN VIVO SECRETION OF A THERAPEUTIC SUBSTANCE

[75] Inventors: Philippe Moullier, Meudon; Olivier Danos, Garches; Jean-Michel Heard; Nicolas Ferry, both of Paris, all of France

[73] Assignee: Institut Pasteur, Paris Cedex, France

[21] Appl. No.: 08/532,814

[22] PCT Filed: Apr. 21, 1994

[86] PCT No.: PCT/FR94/00456

§ 371 Date: Jan. 19, 1996

§ 102(e) Date: Jan. 19, 1996

[87] PCT Pub. No.: WO94/24298

PCT Pub. Date: Oct. 27, 1994

[30] Foreign Application Priority Data

Apr. 21, 1993 [FR] France .................................... 93/04700
Jul. 26, 1993 [FR] France .................................... 93/09185

[51] Int. Cl.⁶ ............................ A01N 63/00; A61K 48/00
[52] U.S. Cl. .................... 424/93.21; 424/93.1; 424/422; 424/423; 435/325; 435/326; 435/382; 435/395; 435/397; 435/400; 604/891.1; 935/62
[58] Field of Search .................... 604/891.1; 424/422, 424/423, 93.1, 93.21; 435/172.3, 320.1, 325, 326, 382, 395, 397–400; 935/62

[56] References Cited

U.S. PATENT DOCUMENTS 4,485,097  11/1984  Bell ........................................... 424/95
4,980,289  12/1990  Temin et al. ............................. 435/235

FOREIGN PATENT DOCUMENTS

92/15676   9/1992  WIPO .

OTHER PUBLICATIONS

JS Cohen (1992) Trends in Biotechnology 10: 87–91.
B Dropulic et al (1994) Human Gene Therapy 5: 927–939.
PA Pizzo et al (1994) Clinical Infectious Diseases 19: 177–196.
ER Kern (1990) In: Antiviral Agents and Viral Diseases of Man, 3rd edition, GJ Galasso et al, eds, pp. 94–95.
Sacramento Bee (Feb. 26, 1994) p. A22.
Sacramento Bee (Nov. 29, 1991) p. B5.
H Collins (Mar. 6, 1993) Philadelphia Inquirer p. A01.
DJ DeNoon (1995) IAC Newsletter DB Accession No. 02944476.
JD Watson et al (1987) Molecular Biology of the Gene, p. 313.
P Moullier et al (1991) J Cell Biochem Supp 15F:242.
G Guillemin et al (1987) J Biomedical Materials Research 21: 557–567.

(List continued on next page.)

Primary Examiner—Bruce R. Campell
Attorney, Agent, or Firm—Oblon, Spivak, McClelland, Maier & Neustadt, P.C.

[57] ABSTRACT

The invention relates to an implant obtained by assembling in vitro various elements in order to form a neo-organ which is introduced preferably in the peritoneal cavity of the recipient. The implant comprises a biocompatible support intended to the biological anchoring of cells; cells having the capacity of expressing and secreting naturally or after recombination a predetermined compound, for example a compound having a therapeutical interest; and a constituent capable of inducing and/or promoting the gelling of said cells. The invention also relates to a kit for the preparation of the implant as well as to a new recombinant retroviral vector comprising a provirus DNA sequence modified in that the genes gag, pol and env have been deleted at least partially so as to obtain a proviral DNA capable of replication. The invention also relates to recombinant cells comprising the new retroviral vector.

35 Claims, 11 Drawing Sheets

OTHER PUBLICATIONS

DG Wallace et al. (1989) J Biomedical Materials Research 23: 931–945.

M Otterlei et al (1991) J Immunotherapy 10: 286–291.

TS Kim et al (1992) Int J Cancer 51: 283–289.

P Moullier et al (1992) J Cell Biochem Supp 16F:62.

JM McPherson et al (1988) Collagen Relat Res 8: 83–100 (Abstract only).

T Hawley et al (1989) Plasmid 22:120–131.

```
TGAAAGACCC CACCTGTAGG TTTGGCAAGC TAGCTTAAGT AACGCCATTT      1

TGCAAGGCAT GGAAAAATAC ATAACTGAGA ATAGAGAAGT TCAGATCAAG     51

GTCAGGAACA GATGGAACAG CTGAATATGG GCCAAACAGG ATATCTGTGG    101

TAAGCAGTTC CTGCCCCGGC TCAGGGCCAA GAACAGATGG AACAGCTGAA    151

TATGGGCCAA ACAGGATATC TGTGGTAAGC AGTTCCTGCC CCGGCTCAGG    201

GCCAAGAACA GATGGTCCCC AGATGCGGTC CAGCCCTCAG CAGTTTCTAG    251

AGAACCATCA GATGTTTCCA GGGTGCCCCA AGGACCTGAA ATGACCCTGT    301

GCCTTATTTG AACTAACCAA TCAGTTCGCT TCTCGCTTCT GTTCGCGCGC    351

TTCTGCTCCC CGAGCTCAAT AAAAGAGCCC ACAACCCCTC ACTCGGGGCG    401

CCAGTCCTCC GATTGACTGA GTCGCCCGGG TACCCGTGTA TCCAATAAAC    451

CCTCTTGCAG TTGCATCCGA CTTGTGGTCT CGCTGTTCCT TGGGAGGGTC    501

TCCTCTGAGT GATTGACTAC CCGTCAGCGG GGGTCTTTCA TTTGGGGGCT    551

CGTCCGGGAT CGGGAGACCC CTGCCCAGGG ACCACCGACC CACCACCGGG    601

AGGTAAGCTG GCCAGCAACT TATCTGTGTC TGTCCGATTG TCTAGTGTCT    651

ATGACTGATT TTATGCGCCT GCGTCGGTAC TAGTTAGCTA ACTAGCTCTG    701

TATCTGGCGG ACCCGTGGTG GAACTGACGA GTTCGGAACA CCCGGCCGCA    751

ACCCTGGGAG ACGTCCCAGG GACTTCGGGG GCCGTTTTTG TGGCCCGACC    801

TGAGTCCAAA AATCCCGATC GTTTTGGACT CTTTGGTGCA CCCCCCTTAG    851
```

*FIG. 1A*

```
AGGAGGGATA TGTGGTTCTG GTAGGAGACG AGAACCTAAA ACAGTTCCCG    901

CCTCCGTCTG AATTTTTGCT TTCGGTTTGG GACCGAAGCC GCGCCGCGCG    951

TCTTGTCTGC TGCAGCATCG TTCTGTGTTG TCTCTGTCTG ACTGTGTTTC   1001

TGTATTTGTC TGAGAATATG GGCCCGCGGG CCAGACTGTT ACCACTCCCT   1051

TAAGTTTGAC CTTAGGTCAC TGGAAAGATG TCGAGCGGAT CGCTCACAAC   1101

CAGTCGGTAG ATGTCAAGAA GAGACGTTGG GTTACCTTCT GCTCTGCAGA   1151

ATGGCCAACC TTTAACGTCG GATGGCCGCG AGACGGCACC TTTAACCGAG   1201

ACCTCATCAC CCAGGTTAAG ATCAAGGTCT TTTCACCTGG CCCGCATGGA   1251

CACCCAGACC AGGTCCCCTA CATCGTGACC TGGGAAGCCT TGGCTTTTGA   1301

CCCCCCTCCC TGGGTCAAGC CCTTTGTACA CCCTAAGCCT CCGCCTCCTC   1351

TTCCTCCATC CGCCCCGTCT CTCCCCCTTG AACCTCCTCG TTCGACCCCG   1401

CCTCGATCCT CCCTTTATCC AGCCCTCACT CCTTCTCTAG GCGCCAAACC   1451

TAAACCTCAA GTTCTTTCTG ACAGTGGGGG GCCGCTCATC GACCTACTTA   1501

CAGAAGACCC CCCGCCTTAT AGGGACCCAA GACCACCCCC TTCCGACAGG   1551

GACGGAAATG GTGGAGAAGC GACCCCTGCG GGAGAGGCAC CGGACCCCTC   1601

CCCAATGGCA TCTCGCCTAC GTGGGAGACG GGAGCCCCCT GTGGCCGACT   1651

CCACTACCTC GCAGGCATTC CCCCTCCGCG CAGGAGGAAA CGGACAGCTT   1701

CAATACTGGC CGTTCTCCTC TTCTGACCTT TACAACTGGA AAAATAATAA   1751
```

*FIG. 1B*

```
CCCTTCTTTT TCTGAAGATC CAGGTAAACT GACAGCTCTG ATCGAGTCTG   1801

TTCTCATCAC CCATCAGCCC ACCTGGGACG ACTGTCAGCA GCTGTTGGGG   1851

ACTCTGCTGA CCGGAGAAGA AAAACAACGG GTGCTCTTAG AGGCTAGAAA   1901

GGCGGTGCGG GGCGATGATG GGCGCCCCAC TCAACTGCCC AATGAAGTCG   1951

ATGCCGCTTT TCCCCTCGAG AATTCTACCG GGTAGGGGAG GCGCTTTTCC   2001

CAAGGCAGTC TGGAGCATGC GCTTTAGCAG CCCCGCTGGC ACTTGGCGCT   2051

ACACAAGTGG CCTCTGGCCT CGCACACATT CCACATCCAC CGGTAGCGCC   2101

AACCGGCTCC GTTCTTTGGT GGCCCCTTCG CGCCACCTTC TACTCCTCCC   2151

CTAGTCAGGA AGTTCCCCCC GCCCGCAGC TCGCGTCGTG CAGGACGTGA    2201

CAAATGGAAG TAGCACGTCT CACTAGTCTC GTGCAGATGG ACAGCACCGC   2251

TGAGCAATGG AAGCGGGTAG GCCTTTGGGG CAGCGGCCAA TAGCAGCTTT   2301

GCTCCTTCGC TTTCTGGGCT CAGAGGCTGG GAAGGGGTGG GTCCGGGGGC   2351

GGGCTCAGGG GCGGGCTCAG GGGCGGGGCG GGCGCGAAGG TCCTCCGGAG   2401

CCCGGCATTC TGCACGCTTC AAAAGCGCAC GTCTGCCGCG CTGTTCTCCT   2451

CTTCCTCATC TCCGGGCCTT TCGACCGGAT CCGGCGATTA GTCCAATTTG   2501

TTAAAGACAG GATATCAGTG GTCCAGGCTC TAGTTTTGAC TCAACAATAT   2551

CACCAGCTGA AGCCTATAGA GTACGAGCCA TAGATAAAAT AAAAGATTTT   2601

ATTTAGTCTC CAGAAAAAGG GGGGAATGAA AGACCCCACC TGTAGGTTTG   2651
```

*FIG. 1C*

```
GCAAGCTAGC TTAAGTAACG CCATTTTGCA AGGCATGGAA AAATACATAA   2701

CTGAGAATAG AGAAGTTCAG ATCAAGGTCA GGAACAGATG GAACAGGGTC   2751

GACCCTAGAG AACCATCAGA TGTTTCCAGG GTGCCCCAAG GACCTGAAAT   2801

GACCCTGTGC CTTATTTGAA CTAACCAATC AGTTCGCTTC TCGCTTCTGT   2851

TCGCGCGCTT CTGCTCCCCG AGCTCAATAA AAGAGCCCAC AACCCCTCAC   2901

TCGGGGCGCC AGTCCTCCGA TTGACTGAGT CGCCCGGGTA CCCGTGTATC   2951

CAATAAACCC TCTTGCAGTT GCATCCGACT TGTGGTCTCG CTGTTCCTTG   3001

GGAGGGTCTC CTCTGAGTGA TTGACTACCC GTCAGCGGGG GTCTTTCATT   3051

TATGTGTCAT AAATATTTCT AATTTTAAGA TAGTATCTCC ATTGGCTTTC   3101

TACTTTTTCT TTTTATTTTT TTTTGTCCTC TGTCTCCATG TGTTGTTGTT   3151

GTTGTTTGTT TGTTTGTTTG TTGGTTGGTT GGTTAATTTT TTTTTAAAGA   3201

TCCTACACTA TAGTTCAAGC TAGACTATTA GCTACTCTGT AACCCAGGGT   3251

GACCTTGAAG TCATGGGTAG CCTGCTGTTT TAGCCTTCCC ACATCTAAGA   3301

TTACAGGTAT GAGCTATCAT TTGGTATAT TGATTGATTG ATTGATTGAT    3351

GTGTGTGTGT GTGATTGTGT TTGTGTGTGT GATTGTGTAT ATGTGTGTAT   3401

GGTTGTGTGT GATTGTGTGT ATGTATGTTT GTGTGTGATT GTGTGTGTGT   3451

GATTGTGCAT GTGTGTGTGT GATGTGTTAG TGTATGATTG TGTGTGTGTG   3501

TGTGTGTGTG TGTGTGTGTG TGTGTGTGTG TGTGTGTTGT GTATATATAT   3551
```

*FIG. 1D*

```
TTATGGTAGT GAGAGGCAAC GCTCCGGCCC AGGCGTCAGG TTGGTTTTTG    3601

AGACAGAGTC TTTCACTTAG CTTGAATTCT TGAAGACGAA AGGGCCTCGT    3651

GATACGCCTA TTTTTATAGG TTAATGTCAT GATAATAATG GTTTCTTAGA    3701

CGTCAGGTGG CACTTTTCGG GGAAATGTGC GCGGAACCCC TATTTGTTTA    3751

TTTTTCTAAA TACATTCAAA TATGTATCCG CTCATGAGAC AATAACCCTG    3801

ATAAATGCTT CAATAATATT GAAAAAGGAA GAGTATGAGT ATTCAACATT    3851

TCCGTGTCGC CCTTATTCCC TTTTTTGCGG CATTTTGCCT TCCTGTTTTT    3901

GCTCACCCAG AAACGCTGGT GAAAGTAAAA GATGCTGAAG ATCAGTTGGG    3951

TGCACGAGTG GGTTACATCG AACTGGATCT CAACAGCGGT AAGATCCTTG    4001

AGAGTTTTCG CCCCGAAGAA CGTTTTCCAA TGATGAGCAC TTTTAAAGTT    4051

CTGCTATGTG GCGCGGTATT ATCCCGTGTT GACGCCGGGC AAGAGCAACT    4101

CGGTCGCCGC ATACACTATT CTCAGAATGA CTTGGTTGAG TACTCACCAG    4151

TCACAGAAAA GCATCTTACG GATGGCATGA CAGTAAGAGA ATTATGCAGT    4201

GCTGCCATAA CCATGAGTGA TAACACTGCG GCCAACTTAC TTCTGACAAC    4251

GATCGGAGGA CCGAAGGAGC TAACCGCTTT TTTGCACAAC ATGGGGGATC    4301

ATGTAACTCG CCTTGATCGT TGGGAACCGG AGCTGAATGA AGCCATACCA    4351

AACGACGAGC GTGACACCAC GATGCCTGCA GCAATGGCAA CAACGTTGCG    4401

CAAACTATTA ACTGGCGAAC TACTTACTCT AGCTTCCCGG CAACAATTAA    4451
```

*FIG. 1E*

```
TAGACTGGAT GGAGGCGGAT AAAGTTGCAG GACCACTTCT GCGCTCGGCC    4501

CTTCCGGCTG GCTGGTTTAT TGCTGATAAA TCTGGAGCCG GTGAGCGTGG    4551

GTCTCGCGGT ATCATTGCAG CACTGGGGCC AGATGGTAAG CCCTCCCGTA    4601

TCGTAGTTAT CTACACGACG GGGAGTCAGG CAACTATGGA TGAACGAAAT    4651

AGACAGATCG CTGAGATAGG TGCCTCACTG ATTAAGCATT GGTAACTGTC    4701

AGACCAAGTT TACTCATATA TACTTTAGAT TGATTTAAAA CTTCATTTTT    4751

AATTTAAAAG GATCTAGGTG AAGATCCTTT TTGATAATCT CATGACCAAA    4801

ATCCCTTAAC GTGAGTTTTC GTTCCACTGA GCGTCAGACC CCGTAGAAAA    4851

GATCAAAGGA TCTTCTTGAG ATCCTTTTTT TCTGCGCGTA ATCTGCTGCT    4901

TGCAAACAAA AAAACCACCG CTACCAGCGG TGGTTTGTTT GCCGGATCAA    4951

GAGCTACCAA CTCTTTTTCC GAAGGTAACT GGCTTCAGCA GAGCGCAGAT    5001

ACCAAATACT GTCCTTCTAG TGTAGCCGTA GTTAGGCCAC CACTTCAAGA    5051

ACTCTGTAGC ACCGCCTACA TACCTCGCTC TGCTAATCCT GTTACCAGTG    5101

GCTGCTGCCA GTGGCGATAA GTCGTGTCTT ACCGGGTTGG ACTCAAGACG    5151

ATAGTTACCG GATAAGGCGC AGCGGTCGGG CTGAACGGGG GGTTCGTGCA    5201

CACAGCCCAG CTTGGAGCGA ACGACCTACA CCGAACTGAG ATACCTACAG    5251

CGTGAGCTAT GAGAAAGCGC CACGCTTCCC GAAGGGAGAA AGGCGGACAG    5301

GTATCCGGTA AGCGGCAGGG TCGGAACAGG AGAGCGCACG AGGGAGCTTC    5351
```

*FIG. 1F*

```
CAGGGGGAAA CGCCTGGTAT CTTTATAGTC CTGTCGGGTT TCGCCACCTC  5401

TGACTTGAGC GTCGATTTTT GTGATGCTCG TCAGGGGGGC GGAGCCTATG  5451

GAAAAACGCC AGCAACGCGG CCTTTTTACG GTTCCTGGCC TTTTGCTGGC  5501

CTTTTGCTCA CATGTTCTTT CCTGCGTTAT CCCCTGATTC TGTGGATAAC  5551

CGTATTACCG CCTTTGAGTG AGCTGATACC GCTCGCCGCA GCCGAACGAC  5601

CGAGCGCAGC GAGTCAGTGA GCGAGGAAGC GGAAGAGCGC CTGATGCGGT  5651

ATTTTCTCCT TACGCATCTG TGCGGTATTT CACACCGCAT ATGGTGCACT  5701

CTCAGTACAA TCTGCTCTGA TGCCGCATAG TTAAGCCAGT ATACACTCCG  5751

CTATCGCTAC GTGACTGGGT CATGGCTGCG CCCCGACACC CGCCAACACC  5801

CGCTGACGCG CCCTGACGGG CTTGTCTGCT CCCGGCATCC GCTTACAGAC  5851

AAGCTGTGAC CGTCTCCGGG AGCTGCATGT GTCAGAGGTT TTCACCGTCA  5901

TCACCGAAAC GCGCGAGGCA GCTGCGGTAA AGCTCATCAG CGTGGTCGTG  5951

AAGCGATTCA CAGATGTCTG CCTGTTCATC CGCGTCCAGC TCGTTGAGTT  6001

TCTCCAGAAG CGTTAATGTC TGGCTTCTGA TAAAGCGGGC CATGTTAAGG  6051

GCGGTTTTTT CCTGTTTGGT CACTGATGCC TCCGTGTAAG GGGGATTTCT  6101

GTTCATGGGG GTAATGATAC CGATGAAACG AGAGAGGATG CTCACGATAC  6151

GGGTTACTGA TGATGAACAT GCCCGGTTAC TGGAACGTTG TGAGGGTAAA  6201

CAACTGGCGG TATGGATGCG GCGGGACCAG AGAAAAATCA CTCAGGGTCA  6251
```

*FIG. 1G*

```
ATGCCAGCGC TTCGTTAATA CAGATGTAGG TGTTCCACAG GGTAGCCAGC    6301

AGCATCCTGC GATGCAGATC CGGAACATAA TGGTGCAGGG CGCTGACTTC    6351

CGCGTTTCCA GACTTTACGA AACACGGAAA CCGAAGACCA TTCATGTTGT    6401

TGCTCAGGTC GCAGACGTTT TGCAGCAGCA GTCGCTTCAC GTTCGCTCGC    6451

GTATCGGTGA TTCATTCTGC TAACCAGTAA GGCAACCCCG CCAGCCTAGC    6501

CGGGTCCTCA ACGACAGGAG CACGATCATG CGCACCCGTG GCCAGGACCC    6551

AACGCTGCCC GAGATGCGCC GCGTGCGGCT GCTGGAGATG GCGGACGCGA    6601

TGGATATGTT CTGCCAAGGG TTGGTTTGCG CATTCACAGT TCTCCGCAAG    6651

AATTGATTGG CTCCAATTCT GGAGTGGTG AATCCGTTAG CGAGGTGCCG     6701

CCGGCTTCCA TTCAGGTCGA GGTGGCCCGG CTCCATGCAC CGCGACGCAA    6751

CGCGGGGAGG CAGACAAGGT ATAGGGCGGC GCCTACAATC CATGCCAACC    6801

CGTTCCATGT GCTCGCCGAG GCGGCATAAA TCGCCGTGAC GATCAGCGGT    6851

CCAGTGATCG AAGTTAGGCT GGTAAGAGCC GCGAGCGATC CTTGAAGCTG    6901

TCCCTGATGG TCGTCATCTA CCTGCCTGGA CAGCATGGCC TGCAACGCGG    6951

GCATCCCGAT GCCGCCGGAA GCGAGAAGAA TCATAATGGG GAAGGCCATC    7001

CAGCCTCGCG TCGCGAACGC CAGCAAGACG TAGCCCAGCG CGTCGGCCGC    7051

CATGCCGGCG ATAATGGCCT GCTTCTCGCC GAAACGTTTG GTGGCGGGAC    7101

CAGTGACGAA GGCTTGAGCG AGGGCGTGCA AGATTCCGAA TACCGCAAGC    7151
```

*FIG. 1H*

```
GACAGGCCGA TCATCGTCGC GCTCCAGCGA AAGCGGTCCT CGCCGAAAAT   7201

GACCCAGAGC GCTGCCGGCA CCTGTCCTAC GAGTTGCATG ATAAAGAAGA   7251

CAGTCATAAG TGCGGCGACG ATAGTCATGC CCCGCGCCCA CCGGAAGGAG   7301

CTGACTGGGT TGAAGGCTCT CAAGGGCATC GGTCGACGCT CTCCCTTATG   7351

CGACTCCTGC ATTAGGAAGC AGCCCAGTAG TAGGTTGAGG CCGTTGAGCA   7401

CCGCCGCCGC AAGGAATGGT GCATGCAAGG AGATGGCGCC CAACAGTCCC   7451

CCGGCCACGG GGCCTGCCAC CATACCCACG CCGAAACAAG CGCTCATGAG   7501

CCCGAAGTGG CGAGCCCGAT CTTCCCCATC GGTGATGTCG GCGATATAGG   7551

CGCCAGCAAC CGCACCTGTG GCGCCGGTGA TGCCGGCCAC GATGCGTCCG   7601

GCGTAGAGCG CCACAGGACG GGTGTGGTCG CCATGATCGC GTAGTCGATA   7651

GTGGCTCCAA GTAGCGAAGC GAGCAGGACT GGGCGGCGGC CAAAGCGGTC   7701

GGACAGTGCT CCGAGAACGG GTGCGCATAG AAATTGCATC AACGCATATA   7751

GCGCTAGCAG CACGCCATAG TGACTGGCGA TGCTGTCGGA ATGGACGATA   7801

TCCCGCAAGA GGCCCGGCAG TACCGGCATA ACCAAGCCTA TGCCTACAGC   7851

ATCCAGGGTG ACGGTGCCGA GGATGACGAT GAGCGCATTG TTAGATTTCA   7901

TACACGGTGC CTGACTGCGT TAGCAATTTA ACTGTGATAA ACTACCGCAT   7951

TAAAGCTTTG CTTAGGAGTT TCCTAATACA TCCCAAACTC AAATATATAA   8001

GCATTTGACT TGTTCTATGC CCTAGGGGGA GGGGGGAAGC TAAGCCAGCT   8051
```

*FIG. 1I*

```
TTTTTTAACA TTTAAAATGT TAATTCCATT TTAAATGCAC AGATGTTTTT   8101

ATTTCATAAG GGTTTCAATG TGCATGAATG TCGCAATATC CTGTTACCAA   8151

AGCTAGTATA AATAAAAATA GATAAACGTG GAAATTACTT AGAGTTTCTG   8201

TCATTAACGT TTCCTTCCTC AGTTGACAAC ATAAATGCGC TGCTGAGAAG   8251

CCAGTTTGCA TCTGTCAGGA TCAATTTCCA TTATGCCAGT CATATTAATT   8301

ACTAGTCAAT TAGTTGATTT TTGACATATA CATGTGAA
```

*FIG. 1J*

SEQUENCE LISTING (1) GENERAL INFORMATION:

(iii) NUMBER OF SEQUENCES: 1

(2) INFORMATION FOR SEQ ID NO:1:

(i) SEQUENCE CHARACTERISTICS:
      (A) LENGTH: 8387 base pairs
      (B) TYPE: nucleic acid
      (C) STRANDEDNESS: double
      (D) TOPOLOGY: linear (ii) MOLECULE TYPE: DNA (genomic)

(xi) SEQUENCE DESCRIPTION: SEQ ID NO:1:

```
TGAAAGACCC CACCTGTAGG TTTGGCAAGC TAGCTTAAGT AACGCCATTT TGCAAGGCAT      60

GGAAAAATAC ATAACTGAGA ATAGAGAAGT TCAGATCAAG GTCAGGAACA GATGGAACAG     120

CTGAATATGG GCCAAACAGG ATATCTGTGG TAAGCAGTTC CTGCCCCGGC TCAGGGCCAA     180

GAACAGATGG AACAGCTGAA TATGGGCCAA ACAGGATATC TGTGGTAAGC AGTTCCTGCC     240

CCGGCTCAGG GCCAAGAACA GATGGTCCCC AGATGCGGTC CAGCCCTCAG CAGTTTCTAG     300

AGAACCATCA GATGTTTCCA GGGTGCCCCA AGGACCTGAA ATGACCCTGT GCCTTATTTG     360

AACTAACCAA TCAGTTCGCT TCTCGCTTCT GTTCGCGCGC TTCTGCTCCC CGAGCTCAAT     420

AAAAGAGCCC ACAACCCCTC ACTCGGGGCG CCAGTCCTCC GATTGACTGA GTCGCCCGGG     480

TACCCGTGTA TCCAATAAAC CCTCTTGCAG TTGCATCCGA CTTGTGGTCT CGCTGTTCCT     540

TGGGAGGGTC TCCTCTGAGT GATTGACTAC CCGTCAGCGG GGGTCTTTCA TTTGGGGGCT     600

CGTCCGGGAT CGGGAGACCC CTGCCCAGGG ACCACCGACC CACCACCGGG AGGTAAGCTG     660

GCCAGCAACT TATCTGTGTC TGTCCGATTG TCTAGTGTCT ATGACTGATT TTATGCGCCT     720

GCGTCGGTAC TAGTTAGCTA ACTAGCTCTG TATCTGGCGG ACCCGTGGTG GAACTGACGA     780

GTTCGGAACA CCCGGCCGCA ACCCTGGGAG ACGTCCCAGG GACTTCGGGG GCCGTTTTTG     840

TGGCCCGACC TGAGTCCAAA AATCCCGATC GTTTTGGACT CTTTGGTGCA CCCCCCTTAG     900

AGGAGGGATA TGTGGTTCTG GTAGGAGACG AGAACCTAAA ACAGTTCCCG CCTCCGTCTG     960

AATTTTTGCT TTCGGTTTGG GACCGAAGCC GCGCCGCGCG TCTTGTCTGC TGCAGCATCG    1020

TTCTGTGTTG TCTCTGTCTG ACTGTGTTTC TGTATTTGTC TGAGAATATG GGCCCGCGGG    1080

CCAGACTGTT ACCACTCCCT TAAGTTTGAC CTTAGGTCAC TGGAAAGATG TCGAGCGGAT    1140

CGCTCACAAC CAGTCGGTAG ATGTCAAGAA GAGACGTTGG GTTACCTTCT GCTCTGCAGA    1200

ATGGCCAACC TTTAACGTCG GATGGCCGCG AGACGGCACC TTTAACCGAG ACCTCATCAC    1260

CCAGGTTAAG ATCAAGGTCT TTTCACCTGG CCCGCATGGA CACCCAGACC AGGTCCCCTA    1320

CATCGTGACC TGGGAAGCCT TGGCTTTTGA CCCCCCTCCC TGGGTCAAGC CCTTTGTACA    1380

CCCTAAGCCT CCGCCTCCTC TTCCTCCATC CGCCCCGTCT CTCCCCCTTG AACCTCCTCG    1440
```

-continued

```
TTCGACCCCG CCTCGATCCT CCCTTTATCC AGCCCTCACT CCTTCTCTAG GCGCCAAACC     1500

TAAACCTCAA GTTCTTTCTG ACAGTGGGGG GCCGCTCATC GACCTACTTA CAGAAGACCC     1560

CCCGCCTTAT AGGGACCCAA GACCACCCCC TTCCGACAGG GACGGAAATG GTGGAGAAGC     1620

GACCCCTGCG GGAGAGGCAC CGGACCCCTC CCCAATGGCA TCTCGCCTAC GTGGGAGACG     1680

GGAGCCCCCT GTGGCCGACT CCACTACCTC GCAGGCATTC CCCCTCCGCG CAGGAGGAAA     1740

CGGACAGCTT CAATACTGGC CGTTCTCCTC TTCTGACCTT TACAACTGGA AAAATAATAA     1800

CCCTTCTTTT TCTGAAGATC CAGGTAAACT GACAGCTCTG ATCGAGTCTG TTCTCATCAC     1860

CCATCAGCCC ACCTGGGACG ACTGTCAGCA GCTGTTGGGG ACTCTGCTGA CCGGAGAAGA     1920

AAAACAACGG GTGCTCTTAG AGGCTAGAAA GGCGGTGCGG GGCGATGATG GGCGCCCCAC     1980

TCAACTGCCC AATGAAGTCG ATGCCGCTTT TCCCCTCGAG AATTCTACCG GGTAGGGGAG     2040

GCGCTTTTCC CAAGGCAGTC TGGAGCATGC GCTTTAGCAG CCCCGCTGGC ACTTGGCGCT     2100

ACACAAGTGG CCTCTGGCCT CGCACACATT CCACATCCAC CGGTAGCGCC AACCGGCTCC     2160

GTTCTTTGGT GGCCCCTTCG CGCCACCTTC TACTCCTCCC CTAGTCAGGA AGTTCCCCCC     2220

GCCCCGCAGC TCGCGTCGTG CAGGACGTGA CAAATGGAAG TAGCACGTCT CACTAGTCTC     2280

GTGCAGATGG ACAGCACCGC TGAGCAATGG AAGCGGGTAG GCCTTTGGGG CAGCGGCCAA     2340

TAGCAGCTTT GCTCCTTCGC TTTCTGGGCT CAGAGGCTGG GAAGGGTTGG GTCCGGGGGC     2400

GGGCTCAGGG GCGGGCTCAG GGGCGGGGCG GGCGCGAAGG TCCTCCGGAG CCCGGCATTC     2460

TGCACGCTTC AAAAGCGCAC GTCTGCCGCG CTGTTCTCCT CTTCCTCATC TCCGGGCCTT     2520

TCGACCGGAT CCGGCGATTA GTCCAATTTG TTAAAGACAG GATATCAGTG GTCCAGGCTC     2580

TAGTTTTGAC TCAACAATAT CACCAGCTGA AGCCTATAGA GTACGAGCCA TAGATAAAAT     2640

AAAAGATTTT ATTTAGTCTC CAGAAAAAGG GGGGAATGAA AGACCCCACC TGTAGGTTTG     2700

GCAAGCTAGC TTAAGTAACG CCATTTTGCA AGGCATGGAA AATACATAA CTGAGAATAG     2760

AGAAGTTCAG ATCAAGGTCA GGAACAGATG GAACAGGGTC GACCCTAGAG AACCATCAGA     2820

TGTTTCCAGG GTGCCCCAAG GACCTGAAAT GACCCTGTGC CTTATTTGAA CTAACCAATC     2880

AGTTCGCTTC TCGCTTCTGT TCGCGCGCTT CTGCTCCCCG AGCTCAATAA AAGAGCCCAC     2940

AACCCCTCAC TCGGGCGCC AGTCCTCCGA TTGACTGAGT CGCCCGGGTA CCCGTGTATC     3000

CAATAAACCC TCTTGCAGTT GCATCCGACT TGTGGTCTCG CTGTTCCTTG GGAGGGTCTC     3060

CTCTGAGTGA TTGACTACCC GTCAGCGGGG GTCTTTCATT TATGTGTCAT AAATATTTCT     3120

AATTTTAAGA TAGTATCTCC ATTGGCTTTC TACTTTTTCT TTTTATTTTT TTTTGTCCTC     3180

TGTCTCCATG TGTTGTTGTT GTTGTTTGTT TGTTTGTTTG TTGGTTGGTT GGTTAATTTT     3240

TTTTTAAAGA TCCTACACTA TAGTTCAAGC TAGACTATTA GCTACTCTGT AACCCAGGGT     3300

GACCTTGAAG TCATGGGTAG CCTGCTGTTT TAGCCTTCCC ACATCTAAGA TTACAGGTAT     3360

GAGCTATCAT TTTGGTATAT TGATTGATTG ATTGATTGAT GTGTGTGTGT GTGATTGTGT     3420

TTGTGTGTGT GATTGTGTAT ATGTGTGTAT GGTTGTGTGT GATTGTGTGT ATGTATGTTT     3480

GTGTGTGATT GTGTGTGTGT GATTGTGCAT GTGTGTGTGT GATGTGTTAG TGTATGATTG     3540

TGTGTGTGTG TGTGTGTGTG TGTGTGTGTG TGTGTGTGTG TGTGTGTTGT GTATATATAT     3600

TTATGGTAGT GAGAGGCAAC GCTCCGGCCC AGGCGTCAGG TTGGTTTTTG AGACAGAGTC     3660

TTTCACTTAG CTTGAATTCT TGAAGACGAA AGGGCCTCGT GATACGCCTA TTTTTATAGG     3720

TTAATGTCAT GATAATAATG GTTCTTAGA CGTCAGGTGG CACTTTTCGG GGAAATGTGC     3780

GCGGAACCCC TATTTGTTTA TTTTTCTAAA TACATTCAAA TATGTATCCG CTCATGAGAC     3840
```

```
AATAACCCTG ATAAATGCTT CAATAATATT GAAAAAGGAA GAGTATGAGT ATTCAACATT    3900

TCCGTGTCGC CCTTATTCCC TTTTTTGCGG CATTTTGCCT TCCTGTTTTT GCTCACCCAG    3960

AAACGCTGGT GAAAGTAAAA GATGCTGAAG ATCAGTTGGG TGCACGAGTG GGTTACATCG    4020

AACTGGATCT CAACAGCGGT AAGATCCTTG AGAGTTTTCG CCCCGAAGAA CGTTTTCCAA    4080

TGATGAGCAC TTTTAAAGTT CTGCTATGTG GCGCGGTATT ATCCCGTGTT GACGCCGGGC    4140

AAGAGCAACT CGGTCGCCGC ATACACTATT CTCAGAATGA CTTGGTTGAG TACTCACCAG    4200

TCACAGAAAA GCATCTTACG GATGGCATGA CAGTAAGAGA ATTATGCAGT GCTGCCATAA    4260

CCATGAGTGA TAACACTGCG GCCAACTTAC TTCTGACAAC GATCGGAGGA CCGAAGGAGC    4320

TAACCGCTTT TTTGCACAAC ATGGGGGATC ATGTAACTCG CCTTGATCGT TGGGAACCGG    4380

AGCTGAATGA AGCCATACCA AACGACGAGC GTGACACCAC GATGCCTGCA GCAATGGCAA    4440

CAACGTTGCG CAAACTATTA ACTGGCGAAC TACTTACTCT AGCTTCCCGG CAACAATTAA    4500

TAGACTGGAT GGAGGCGGAT AAAGTTGCAG GACCACTTCT GCGCTCGGCC CTTCCGGCTG    4560

GCTGGTTTAT TGCTGATAAA TCTGGAGCCG GTGAGCGTGG GTCTCGCGGT ATCATTGCAG    4620

CACTGGGGCC AGATGGTAAG CCCTCCCGTA TCGTAGTTAT CTACACGACG GGGAGTCAGG    4680

CAACTATGGA TGAACGAAAT AGACAGATCG CTGAGATAGG TGCCTCACTG ATTAAGCATT    4740

GGTAACTGTC AGACCAAGTT TACTCATATA TACTTTAGAT TGATTTAAAA CTTCATTTTT    4800

AATTTAAAAG GATCTAGGTG AAGATCCTTT TTGATAATCT CATGACCAAA ATCCCTTAAC    4860

GTGAGTTTTC GTTCCACTGA GCGTCAGACC CCGTAGAAAA GATCAAAGGA TCTTCTTGAG    4920

ATCCTTTTTT TCTGCGCGTA ATCTGCTGCT TGCAAACAAA AAAACCACCG CTACCAGCGG    4980

TGGTTTGTTT GCCGGATCAA GAGCTACCAA CTCTTTTTCC GAAGGTAACT GGCTTCAGCA    5040

GAGCGCAGAT ACCAAATACT GTCCTTCTAG TGTAGCCGTA GTTAGGCCAC CACTTCAAGA    5100

ACTCTGTAGC ACCGCCTACA TACCTCGCTC TGCTAATCCT GTTACCAGTG GCTGCTGCCA    5160

GTGGCGATAA GTCGTGTCTT ACCGGGTTGG ACTCAAGACG ATAGTTACCG GATAAGGCGC    5220

AGCGGTCGGG CTGAACGGGG GGTTCGTGCA CACAGCCCAG CTTGGAGCGA ACGACCTACA    5280

CCGAACTGAG ATACCTACAG CGTGAGCTAT GAGAAAGCGC CACGCTTCCC GAAGGGAGAA    5340

AGGCGGACAG GTATCCGGTA AGCGGCAGGG TCGGAACAGG AGAGCGCACG AGGGAGCTTC    5400

CAGGGGGAAA CGCCTGGTAT CTTTATAGTC CTGTCGGGTT TCGCCACCTC TGACTTGAGC    5460

GTCGATTTTT GTGATGCTCG TCAGGGGGGC GGAGCCTATG GAAAAACGCC AGCAACGCGG    5520

CCTTTTTACG GTTCCTGGCC TTTTGCTGGC CTTTTGCTCA CATGTTCTTT CCTGCGTTAT    5580

CCCCTGATTC TGTGGATAAC CGTATTACCG CCTTTGAGTG AGCTGATACC GCTCGCCGCA    5640

GCCGAACGAC CGAGCGCAGC GAGTCAGTGA GCGAGGAAGC GGAAGAGCGC CTGATGCGGT    5700

ATTTTCTCCT TACGCATCTG TGCGGTATTT CACACCGCAT ATGGTGCACT CTCAGTACAA    5760

TCTGCTCTGA TGCCGCATAG TTAAGCCAGT ATACACTCCG CTATCGCTAC GTGACTGGGT    5820

CATGGCTGCG CCCCGACACC CGCCAACACC CGCTGACGCG CCCTGACGGG CTTGTCTGCT    5880

CCCGGCATCC GCTTACAGAC AAGCTGTGAC CGTCTCCGGG AGCTGCATGT GTCAGAGGTT    5940

TTCACCGTCA TCACCGAAAC GCGCGAGGCA GCTGCGGTAA AGCTCATCAG CGTGGTCGTG    6000

AAGCGATTCA CAGATGTCTG CCTGTTCATC CGCGTCCAGC TCGTTGAGTT TCTCCAGAAG    6060

CGTTAATGTC TGGCTTCTGA TAAAGCGGGC CATGTTAAGG GCGGTTTTTT CCTGTTTGGT    6120

CACTGATGCC TCCGTGTAAG GGGGATTTCT GTTCATGGGG GTAATGATAC CGATGAAACG    6180

AGAGAGGATG CTCACGATAC GGGTTACTGA TGATGAACAT GCCCGGTTAC TGGAACGTTG    6240
```

```
TGAGGGTAAA CAACTGGCGG TATGGATGCG GCGGGACCAG AGAAAAATCA CTCAGGGTCA    6300
ATGCCAGCGC TTCGTTAATA CAGATGTAGG TGTTCCACAG GGTAGCCAGC AGCATCCTGC    6360
GATGCAGATC CGGAACATAA TGGTGCAGGG CGCTGACTTC CGCGTTTCCA GACTTTACGA    6420
AACACGGAAA CCGAAGACCA TTCATGTTGT TGCTCAGGTC GCAGACGTTT TGCAGCAGCA    6480
GTCGCTTCAC GTTCGCTCGC GTATCGGTGA TTCATTCTGC TAACCAGTAA GGCAACCCCG    6540
CCAGCCTAGC CGGGTCCTCA ACGACAGGAG CACGATCATG CGCACCCGTG GCCAGGACCC    6600
AACGCTGCCC GAGATGCGCC GCGTGCGGCT GCTGGAGATG GCGGACGCGA TGGATATGTT    6660
CTGCCAAGGG TTGGTTTGCG CATTCACAGT TCTCCGCAAG AATTGATTGG CTCCAATTCT    6720
TGGAGTGGTG AATCCGTTAG CGAGGTGCCG CCGGCTTCCA TTCAGGTCGA GGTGGCCCGG    6780
CTCCATGCAC CGCGACGCAA CGCGGGGAGG CAGACAAGGT ATAGGGCGGC GCCTACAATC    6840
CATGCCAACC CGTTCCATGT GCTCGCCGAG GCGGCATAAA TCGCCGTGAC GATCAGCGGT    6900
CCAGTGATCG AAGTTAGGCT GGTAAGAGCC GCGAGCGATC CTTGAAGCTG TCCCTGATGG    6960
TCGTCATCTA CCTGCCTGGA CAGCATGGCC TGCAACGCGG GCATCCCGAT GCCGCCGGAA    7020
GCGAGAAGAA TCATATGGGG AAGGCCATCC AGCCTCGCGT CGCGAACGCC AGCAAGACGT    7080
AGCCCAGCGC GTCGGCCGCC ATGCCGGCGA TAATGGCCTG CTTCTCGCCG AAACGTTTGG    7140
TGGCGGGACC AGTGACGAAG GCTTGAGCGA GGGCGTGCAA GATTCCGAAT ACCGCAAGCG    7200
ACAGGCCGAT CATCGTCGCG CTCCAGCGAA AGCGGTCCTC GCCGAAAATG ACCCAGAGCG    7260
CTGCCGGCAC CTGTCCTACG AGTTGCATGA TAAAGAAGAC AGTCATAAGT GCGGCGACGA    7320
TAGTCATGCC CCGCGCCCAC CGGAAGGAGC TGACTGGGTT GAAGGCTCTC AAGGGCATCG    7380
GTCGACGCTC TCCCTTATGC GACTCCTGCA TTAGGAAGCA GCCCAGTAGT AGGTTGAGGC    7440
CGTTGAGCAC CGCCGCCGCA AGGAATGGTG CATGCAAGGA GATGGCGCCC AACAGTCCCC    7500
CGGCCACGGG GCCTGCCACC ATACCCACGC CGAAACAAGC GCTCATGAGC CCGAAGTGGC    7560
GAGCCCGATC TTCCCCATCG GTGATGTCGG CGATATAGGC GCCAGCAACC GCACCTGTGG    7620
CGCCGGTGAT GCCGGCCACG ATGCGTCCGG CGTAGAGCGC CACAGGACGG GTGTGGTCGC    7680
CATGATCGCG TAGTCGATAG TGGCTCCAAG TAGCGAAGCG AGCAGGACTG GGCGGCGGCC    7740
AAAGCGGTCG GACAGTGCTC CGAGAACGGG TGCGCATAGA AATTGCATCA ACGCATATAG    7800
CGCTAGCAGC ACGCCATAGT GACTGGCGAT GCTGTCGGAA TGGACGATAT CCCGCAAGAG    7860
GCCCGGCAGT ACCGGCATAA CCAAGCCTAT GCCTACAGCA TCCAGGGTGA CGGTGCCGAG    7920
GATGACGATG AGCGCATTGT TAGATTTCAT ACACGGTGCC TGACTGCGTT AGCAATTTAA    7980
CTGTGATAAA CTACCGCATT AAAGCTTTGC TTAGGAGTTT CCTAATACAT CCCAAACTCA    8040
AATATATAAG CATTTGACTT GTTCTATGCC CTAGGGGAG GGGGGAAGCT AAGCCAGCTT    8100
TTTTTAACAT TTAAAATGTT AATTCCATTT TAAATGCACA GATGTTTTTA TTTCATAAGG    8160
GTTTCAATGT GCATGAATGT CGCAATATCC TGTTACCAAA GCTAGTATAA ATAAAAATAG    8220
ATAAACGTGG AAATTACTTA GAGTTTCTGT CATTAACGTT TCCTTCCTCA GTTGACAACA    8280
TAAATGCGCT GCTGAGAAGC CAGTTTGCAT CTGTCAGGAT CAATTTCCAT TATGCCAGTC    8340
ATATTAATTA CTAGTCAATT AGTTGATTTT TGACATATAC ATGTGAA                 8387
```

BIOCOMPATIBLE IMPLANT FOR THE EXPRESSION AND IN VIVO SECRETION OF A THERAPEUTIC SUBSTANCE

The invention relates to a biocompatible implant for the expression of defined substances in man or in animals, in particular for the anchoring of the recombinant cells of the invention.

The present invention also relates to retroviral vectors for the preparation of recombinant cells capable of being implanted in vivo for a therapeutic purpose.

STATE OF THE ART

The in vivo introduction of implants capable of expressing defined substances for example for therapeutic purposes necessitates the use of efficacious agents as regards the desired therapeutic or prophylactic objective and that the organism into which the implant is introduced has the capacity to tolerate it in the relatively long-term.

The earlier international patent application published under the number 92/15676 described agents to obtain in vivo the expression of defined nucleotide sequences for the purpose of a therapeutic treatment of diseases resulting from a genetic anomaly. This international application 92/15676 proposes the use of fibroblasts genetically modified by a retroviral vector for the purpose of implanting them in the connective tissue of the skin of the subject to be treated.

The nucleotide sequence whose expression is desired in this earlier international application is placed under the control of the LTR (Long Terminal Repeat) sequence of the retroviral vector and/or under the control of inducible or constitutive exogenous promoters, the LTR sequence of the retrovirus being nonetheless conserved when the exogenous promoter is present.

SUMMARY OF THE INVENTION

The invention proposes agents making it possible to achieve in vivo the expression of a selected nucleotide sequence under conditions such that this expression is obtained over a period of several months, preferably more than 6 months, in a manner such that the product of the nucleotide sequence expressed is present in sufficient quantity and under conditions suitable for the production of a desired therapeutic effect in vivo.

The agents defined in the present application make it possible to achieve the expression and the secretion of a protein, glycoprotein or a peptide of biological interest to justify its therapeutic use in vivo.

The invention also relates to the use of biocompatible materials as supports for the introduction into man or animals of cells for example recombinant cells of the invention defined below, starting from which it is desired to produce a defined molecule in particular for therapeutic purposes.

The preparation of implants requires such supports suitable for being placed in contact with cells and various factors promoting the adhesion of these cells to the support if necessary, under conditions such that the different constituents present conserve their principal natural structural and functional properties.

These biocompatible supports whether of biological origin or not may or may not be resorbable by the host into which they are introduced.

The invention also concerns retroviral vectors having the capacity to infect cells, and in particular eukaryotic cells, as well as the recombinant cells including these vectors. The recombinant cells of the invention may be administered or implanted in a patient, thus producing in vivo a protein or any expression product of a defined nucleotide sequence inserted into the retroviral vector.

The inventors have examined which are the parameters which, at various levels, would make it possible to express in vivo a defined nucleotide sequence so as to improve the expression of the nucleotide sequence inserted in the vector in order to obtain a therapeutic effect, if necessary of long duration.

Thus, they have demonstrated that when the exogenous nucleotide sequence whose expression is desired is advantageously placed in the vector intended for the infection of the cells under the control of an inducible or constitutive exogenous promoter, the LTR sequence internal to the retroviral vector must then be partially deleted. The deletion must be sufficient to impair the transcription of the mRNA.

DETAILED DESCRIPTION OF THE INVENTION

Biocompatible Implant

The implant or new-organ of the invention is obtained by the process which consists in the in vitro assembly of various elements in order to form an implant which is introduced preferably into the peritoneal cavity of the recipient. Other implantation sits can be used such as the perirenal space, the skin. In vivo the implant gives rise to a connective tissue formed de novo, which is vascularized and unmodified over the course of time.

In general, the implant of the invention is characterized in that it comprises:

- a biocompatible support making possible the biological anchoring of cells;
- cells having the capacity to express and secrete naturally or after recombination a defined substance, for example, a substance of therapeutic interest; and
- a constituent capable of inducing and/or promoting the gelation of said cells.

In particular, the elements participating in the assembly of the in vitro implant are the following:

1) A rigid support. It may be prepared from different biomaterials: PTFE, coral, cross-linked collagen fibers;
2) A collagen gel. It is possible to use rat tail collagen, bovine collagen, human collagen; and
3) Genetically modified cells, preferably the recombinant cells of the present invention which are described in detail below.

Hence the object of the invention is an implant or neo-organ characterized in that it comprises a biocompatible rigid support, in particular a rigid support made of PFTE or of biological origin, making possible the biological anchoring of cells previously placed or not placed in contact with constituents capable of inducing and/or promoting their inclusion within a gel-forming matrix, said cells being chosen for their capacity to express and secrete naturally or after recombination a defined substance, for example a substance of therapeutic interest.

The expression "biological anchoring" means that the cells contained in the implant can bind to the surface of the biocompatible support or, in certain cases, penetrate into the interior of this support.

This binding of the cells to the support is made possible in particular by the presence of constituents capable of inducing and/or promoting the inclusion of the cells within a matrix having the constitution of a gel.

This inclusion in the matrix, called gelation, permits the organization of the cells in a three-dimensional structure in an amorphous environment, not giving rise in vivo to prolonged inflammation.

According to a first embodiment of the invention, the implant obtained is constituted on the one hand of a biocompatible material such as a support consisting of a synthetic biocompatible material, in particular polytetrafluoroethylene fibers (PTFE) or a support consisting of a calcium-based material, in particular a material based on calcium carbonate, of biological origin, preferably coral and, on the other hand, a gel optionally loaded with cells expressing the substance of interest, in particular recombinant cells.

The invention also relates to a method of preparation of the implant. The method comprises the steps of:

placing the biocompatible support in contact with said cells and a constituent capable of inducing and/or promoting their gelation;

incubation of the preparation obtained in the preceding step in order to obtain the gelation of said constituents;

culture of cells thus obtained under conditions permitting their binding to the gelled constituents; and recovery of the implant thus obtained.

a) Implant Consisting of a Synthetic Biocompatible Material

The object of the invention is an implant or neo-organ characterized in that it comprises cells expressing the substance of interest, in combination with polytetrafluoroethylene (PTFE) fibers and collagen. On being introduced in vivo, such an implant is capable of constituting a vascularized neo-organ, individualized within a tissue.

Advantageously, the implant such as described above comprises in addition a growth factor, for example the bFGF (basic Fibroblast Growth Factor). This growth factor promotes the vascularization of the neo-organ when the latter is implanted in vivo.

Preferably, the neo-organ is introduced into the peritoneal cavity of the patient in whom it is desired to obtain the expression of the exogenous nucleotide sequence contained in the vector of the invention. This localization of the neo-organ is favourable for the development of its vascularization and to its maintenance in an individualized form in this organ. The implantation of the neo-organ comprising recombinant cells according to the invention may be permanent or, on the contrary, temporary, it being possible in this latter case to withdraw the neo-organ after a given time of implantation.

Furthermore, the invention relates to a process for the preparation of an implant defined above, comprising the steps of placing recombinant cells in contact with a solution of collagen and PTFE fibers preferably previously treated with collagen and optionally with an angiogenic growth factor, incubation of the preparation obtained in the preceding step in order to obtain the gelation of the collagen, culture of the cells thus obtained for a time sufficient to allow the cells to bind to the collagen fibers, recovery of the implant thus obtained.

b) Implant Consisting of a Biocompatible Material of Biological Origin

Preferably, the material used is a high porosity coral, i.e. it possesses a porosity such as that described in the French patent No. 2 460 657. It may also be a powder of sufficient porosity to make it possible to obtain a solid framework for the purpose of constituting a cellular network comprising or not a biological support such as collagen. In this case in which the coral is replaced by collagen, cross-linked or not, this latter may also serve both as support and as matrix promoting the biological gelation for the constitution of the network of cells.

According to an advantageous embodiment of the invention the high porosity coral used is of the spherical type.

According to another embodiment, the implant consists of a support of biological origin forming a solid matrix, said support containing:

collagen with variable cross-linking, for example in the form of fibers or sponges such as those sold under the trade marks Hemostagene® or Paroguide®;

powered or fragmented bone; or carbohydrate-based polymers such as dextran or hyaluronic acid.

According to an advantageous embodiment of the invention, the solid framework of biological origin is capable of being resorbed in vivo.

The implant thus constituted allows the in vivo formation of an individualized and, if necessary, stable neo-organ in which the biological support is capable of being progressively resorbed leaving in place a structure containing a vascularized connective tissue of a form quite comparable to that of the implant, this neo-organ having, however, optionally a reduced volume compared with the volume of the original implant.

A particularly preferred implant in the framework of the invention is such that the constituents capable of inducing and/or promoting the gelation of the cells are for example uncross-linked collagen or alginates.

In particular, recourse will be had to type I collagen, for example, in particular at a concentration of 1.5 mg/ml.

Other constituents for gelling the cells may naturally be used provided that they have the desired functional property and that they exhibit the properties of biocompatibility required in order to be introduced in vivo in man or animals.

c) Use of the Implant of the Invention

An implant particularly suited to the realization of the invention is additionally characterized in that the cells are recombinant cells carrying genetic information foreign to their genome and capable of expressing this additional information in vivo and having the capacity to be tolerated immunologically by an organism to which they might be administered.

In a preferred manner, an implant according to the invention is characterized in that the recombinant cells are modified by a vector containing one or more exogenous nucleotide sequences, coding for an antigen or antigenic determinant or coding for a polypeptide or glycoprotein, soluble in serum, for example a polypeptide or a glycoprotein of therapeutic interest, in particular a hormone, a structural protein or glycoprotein or a metabolic protein or glycoprotein or a viral protein or glycoprotein or a protein having the properties of an antibody or antibody fragment.

In a preferred manner, the implant contains in addition one or more angiogenic factors, in particular bFGF, preferably incorporated during the placing of the biocompatible support in contact with the cells and the constituent capable of inducing and/or promoting their gelation.

The binding of the angiogenic factor, for example bFGF, is promoted by the presence of the gelling agent.

This agent contributes to the stable binding of the angiogenic factors to the support of biological origin of the implant.

In a particularly advantageous manner, the implant also contains heparin or a heparin derivative such as heparan sulfate or heparin fractions.

Heparin and its derivatives are capable of binding to the constituents promoting gelation and thus of increasing the affinity of the angiogenic factors for the constituents responsible for gelation. In particular, heparin binds to collagen and thus increases the affinity of bFGF for collagen.

The implant according to the invention may be employed in a permanent or temporary fashion for use in man or animals. In fact, its capacity to constitute in vivo an individualized neo-organ makes it possible to withdraw it if necessary.

In a particularly valuable manner an implant according to the invention can be used for:

- the treatment of genetic diseases, in particular for the treatment of lysosomal overload, hemophilia A or hemophilia B, of beta-thalassemia, the exogenous nucleotide sequence contained in the recombinant cells corresponding respectively to those which code for beta-glucuronidase, for the factor VIII, factor IX or erythropoietin, or for an active part of these sequences;
- the treatment of acquired diseases, for example for the treatment of viral diseases, in particular for the treatment of an infection due to the HIV retrovirus for example by the expression and secretion into the serum of soluble CD4 molecules or of a soluble anti-viral protein;
- the treatment of tumors, the exogenous nucleotide sequence contained in the recombinant cells coding for a substance capable of promoting or enhancing the immune response against the tumor cells.

The object of the invention is also a composition characterized in that it contains an implant according to the invention and one or more other constituents such as for example an antigen, an adjuvant in particular for vaccination.

The agents described in the invention thus make it possible to envisage the treatment of genetic or acquired diseases over a long period, more than several months, and do so without the repeated administration of the expression product of the exogenous nucleotide sequence whose therapeutic activity is desired. Furthermore, the agents described in the invention lead to the production in the form of a secreted protein of a quantity of expression product of the exogenous nucleotide sequence sufficient to have a therapeutic effect in vivo.

Another application of the recombinant cells according to the invention or compositions or implants containing them relates to the preparation of antibodies against the expression product of the exogenous nucleotide sequence contained in the vector introduced into the recombinant cells. Preferably, these antibodies are produced in vivo when the recombinant cells are implanted in an organism.

This use makes it possible for example to produce antibodies against an antigen neither whose amino acid sequence nor necessarily the DNA or cDNA sequence has been identified. Depending on the effect desired, the introduction of the recombinant vector according to the invention will be made into a defined cell type.

Similarly, the invention permits the in vivo production of antibodies against a defined antigen for example for the purposes of vaccinating a patient.

Recombinant cells such as those described below or compositions or implants containing them may also be used for the treatment of tumors, the exogenous nucleotide sequence contained in the recombinant cells coding for a substance capable of promoting or enhancing the immune response against the tumor cells.

As a particular instance, the recombinant cells utilizable for the treatment of tumors may be cells obtained by recombination of tumor cells taken from a patient with a retroviral vector complying with the specifications given in the following pages.

Kit According to the Invention

The invention also includes a kit for the preparation of an implant for achieving in vivo the expression and secretion by cells of a substance for producing the desired therapeutic effect. The kit of the invention usually contains:

- a biocompatible support making possible the anchoring of said cells; and
- a constituent capable of inducing and/or promoting the gelation of said cells.

In particular, the biocompatible support comprises at least one of the ingredients chosen from among the group including PTFE or a support of biological origin, particularly a calcium-based, and in particular a calcium carbonate-based, support of biological origin, and preferably coral. The constituent capable of inducing and/or promoting the gelation of the cells is preferably collagen, in particular type I collagen, and preferably at a concentration of the order of 1.5 mg/ml.

The kit according to the invention may also include a DNA comprising a sequence coding for the substance expressed and secreted by said cells. This DNA may be used to transform the cells taken from the patient to be treated.

More particularly, the DNA forming part of the kit is a retroviral vector such as that described below.

The kit may also contain cells having the capacity to express and secrete naturally or after recombination a defined substance, for example a substance of therapeutic interest.

Retroviral Vector and Recombinant Cells a) Retroviral Vector

A novel recombinant retroviral vector according to the invention is characterized in that it comprizes:

a provirus DNA sequence modified in that:

the gag, pol and env genes have been deleted at least in part in order to obtain a proviral DNA incapable of self-replication, this DNA in addition not being able to recombine to form a wild-type virus;

the LTR sequence bears a deletion in the U3 sequence such that transcription of the mRNA it controls is significantly reduced, by at least 10 fold for example, and this recombinant retroviral vector comprising in addition an exogenous nucleotide sequence under control of a promoter for example an exogenous inducible or constitutive promoter.

The principal elements forming this vector are described below in detail.

1) Proviral DNA

A "proviral DNA sequence" is a sequence of DNA transcribed from the genomic RNA of the virus when it is integrated in the host cells of the virus. The proviral DNA thus comprises sequences coding for the gag, pol and env proteins of the retrovirus which correspond respectively to the nucleoproteins, polymerases, envelope proteins and glycoproteins.

The retroviral vector according to the invention is such that the gag, pol and env genes of the proviral DNA have been deleted at least in part in order to obtain a proviral DNA incapable of self-replication, this DNA in addition being unable to recombine to form a wild-type virus.

The proviral DNA also bears sequences called LTR (Long Terminal Repeat) which bear regions called R, U3 and U5. These sequences of the LTR region are involved in the replication cycle of the retrovirus.

The LTR sequence of the proviral DNA has also been mutated by deletion, for example in its U3 part; this deletion affects the functions of the internal enhancer of the LTR region. Furthermore, this deletion makes it possible to diminish and preferably to neutralize the transcriptional effect of the LTR region by conserving the capacity of the exogenous promoter to promote and control the expression of the exogenous nucleotide sequence contained in the retroviral vector.

It is also possible to envisage the deletion of all of the sequence constituting the promoter and the enhancer. However, such a deletion has the disadvantage of being accompanied by a considerable diminution of the vector titers.

According to a variant of the embodiment of the invention, the proviral sequence upstream from the exogenous promoter is the nucleotide sequence situated between nucleotides 1 and about 1500 according to the numbering of the sequence shown in FIG. 1. This sequence upstream from the promoter essentially lacks the entire complement of the gag, pol and env genes of the proviral sequence.

The exogenous nucleotide sequence is advantageously inserted under the control of the exogenous promoter in the place of the deleted gag, pol and env sequences.

When the promoter is the PGK-1 promoter described below, the exogenous nucleotide sequence is advantageously inserted at the BamHI site downstream from this promoter.

2) Exogenous Nucleotide Sequence

An "Exogenous nucleotide sequence" according to the invention is a sequence which is not expressed naturally in a cell in which the retroviral vector of the invention is introduced or is expressed there in insufficient quantity or is one which it is desired to produce in greater quantity than is normally expressed. This defective or insufficient expression results from the nature of the cell or occurs because of a disease affecting this cell in a given individual.

In a preferred manner, the "exogenous nucleotide sequence" codes for a defined polypeptide. By "polypeptide" is meant any amino acid sequence irrespective of its size, this expression comprising proteins and peptides. The polypeptide may be in a glycosylated or non-glycosylated form.

3) Exogenous Promoter

The promoter used for the construction of recombinant retroviruses according to the invention is advantageously exogenous with respect to the sequence whose expression it controls in the sense that it is not naturally associated with it. It is also possible to use the promoter of the transferred exogenous gene.

The promoter used in the vector of the invention may be of the inducible or constitutive type. This exogenous promoter controls the expression of the exogenous nucleotide sequence. The promoter may optionally be accompanied by a regulatory nucleic acid sequence for example an "enhancer" which would serve to regulate its activity.

In the case of inducible promoters, promoters such as the Mx promoter in mice, the promoters including a tetracycline operator or even promoters regulated by hormones, in particular steroid hormones, may also be used. As regards the so-called "constitutive" promoters, the use of active internal promoters in resting fibroblasts such as the PGK promoter or another promoter of the housekeeping gene is preferred.

In a particularly advantageous manner for the construction of the retroviral vector according to the invention, the exogenous constitutive promoter is a promoter without a TATA box and in particular the promoter of the phosphoglycerate kinase gene (PGK-1). This promoter is either the mouse promoter or the human promoter as described by Adra et al. (Gene 60, 1987, 65–74).

The insertion of the PGK-1 promoter into a retroviral vector makes possible the transfer of the gene into skin fibroblasts for example and the stable expression at high level and for the very long term of this gene after the fibroblasts have been implanted in vivo in a recipient, a mammal for example.

Other constitutive promoters may be used in place of the PGK-1 promoter. In general, recourse will be had to a promoter active in the cells which it is desired to transform with the retroviral vector and in particular active promoters in quiescent fibroblasts, for example promoters preceding the genes for the cytoskeleton. It is also possible to mention the promoter of beta-actin. (Kort et al., 1983, Nucl. Acids Res. 11: 8287–8301) or the promoter of the vimentin gene (Rettlez et Basenga (1987), Mol. Cell. Biol. 7: 1676–1685). The promoter used may lack a "TATA box".

4) Preferential Constructions of the Retroviral Vector

A first particular retroviral vector in the framework of the invention is such that an exogenous nucleotide sequence and an exogenous constitutive promoter as well as the proviral DNA sequence are borne by a plasmid. As an example, these sequences may be borne by the plasmid pBR322 which allows the introduction of the DNA into the cell lines in which it is desired to produce the vector.

According to another advantageous embodiment of the invention a vector complying with the preceding specifications is in addition characterized in that the proviral DNA is derived from the Mo-MuLV retrovirus. Other retroviruses of the MuLV family may be used and mention should be made, for example, of the HaSV or F-MuLV retroviruses.

Preferably, the sequences of the pol and env genes of the proviral DNA are completely deleted. In this case, the sequence of the gag gene may also be entirely deleted or, on the other hand, be conserved in part, provided that the proviral DNA thus constituted is no longer capable of replication.

Advantageously, a retroviral vector such as previously defined is characterized in that the U3 region of the LTR3' fragment is deleted at nucleotide 2797 of FIG. 1. This deletion corresponds to a deletion of a fragment situated between nucleotides 7935 and 8113 according to the numbering of the sequence published by Shinnick et al. (Nature 293, 543–548, 1981). This deleted fragment of the U3 sequence of the LTR3' contains the enhancer region of the LTR.

Preferably, a retroviral vector according to the invention is a type pM48 vector derived from the Moloney virus in which the viral "enhancer" localized in V3 has been deleted and which contains an internal promoter active in resting fibroblasts, preferably the PGK promoter or another promoter of the housekeeping gene, such as the vector shown in FIG. 2, modified by the exogenous nucleotide sequence at the BamHI site.

The retroviral vector M48 LacZ (also designated by the expression pM48 LacZ) was deposited with the CNCM (Collection Nationale de Culture de Microorganismes, Paris—France) under the No.I-1298 on Apr. 16, 1993.

This vector is derived from the vector pM48 and is characterized in that it contains downstream from the exogenous constitutive promoter a BamHI fragment of the gene for beta-galactosidase.

This fragment of the beta-galactosidase gene may easily be deleted and replaced by an exogenous nucleotide sequence of interest, for example a sequence coding for a protein or a glycoprotein capable of having therapeutic value or against the protein product of which it would be desired for example to obtain antibodies.

A retroviral vector of the invention may also contain a sequence capable of enhancing the transcriptional activity of the promoter either constitutively or inducibly. The vector may contain an enhancer sequence upstream from the exogenous promoter.

b) Recombinant Cells

Moreover, the invention relates to recombinant cells characterized in that they are cells having the capacity to be tolerated immunologically by an organism in which they might be implanted, modified by a retroviral vector complying with one of the preceding specifications.

Such cells may be cells derived from the organism into which they are to be implanted after recombination by transduction with the vector of the invention or cells lacking at their surface antigens recognized by the immune system of the organism into which they are implanted.

They may also be endothelial cells, myoblasts, muscle cells or tumor cells irradiated or treated according to other procedures to prevent their proliferation and taken from the patient whose genetic make-up it is desired to modify so that they may counteract the development of the tumor.

Preferably, these recombinant cells are recombinant fibroblasts and in particular skin fibroblasts. Preferably, they are autologous fibroblasts with respect to the patient in whom it is desired to implant them after their modification by a vector according to the invention. Fibroblasts prepared from other organisms may be used such as for example fibroblasts isolated from an umbilical cord. The genetically modified fibroblasts used in the context of the present invention are not immortalized fibroblasts.

These cells may be modified by a recombinant vector coding for a defined polypeptide, said vector permitting the expression of the foreign DNA in the cells. They may also be modified by the methods of so-called homologous recombination. The penetration of the vector into the cells is carried out by using electroporation or precipitation with calcium phosphate or also by any other method implicated in the entry of a nucleic acid either alone or through the intermediary of a recombinant virus, for example.

By "recombined cells" is also meant tumor autologous cells irradiated prior to their introduction into the gel, having the capacity to maintain at their surface tumor antigens accessible to the immune system of the host into which the implant according to the invention has been introduced.

The recombinant cells of the invention are also obtained either by infection of the cells to be modified with a retroviral vector of the invention, or by other transduction methods involving naked DNA, DNA-proteins complex or an adenoviral vector. In the case of an infection with a retroviral vector, the sequence coding for the polypeptide whose expression (exogenous nucleotide sequence) is desired is introduced into the proviral DNA.

In a preferred manner, the recombinant cells are modified by a vector containing one or more exogenous nucleotide sequence(s) coding for an antigen or an antigenic determinant or coding for a polypeptide or a glycoprotein, soluble in the serum, for example a polypeptide or a glycoprotein of therapeutic interest, in particular a hormone, a structural protein or glycoprotein or a metabolic protein or glycoprotein or a viral protein or glycoprotein or a protein having the properties of an antibody or an antibody fragment.

As an example, this exogenous nucleotide sequence codes for beta-glucuronidase or another lysosomal enzyme such as alpha-iduronidase or arylsulfatase B, a coagulation factor such as factor VIII or factor IX, erythropoietin or any active part of one of these proteins.

Other advantages and characteristics of the invention will become apparent in the Examples and the Figures which follow.

BRIEF DESCRIPTION OF THE DRAWINGS

FIG. 1: nucleotide sequence (SEQ ID NO:1) of the vector M48;

EXAMPLES

Preparation of the Recombinant Vector

Figure 2:
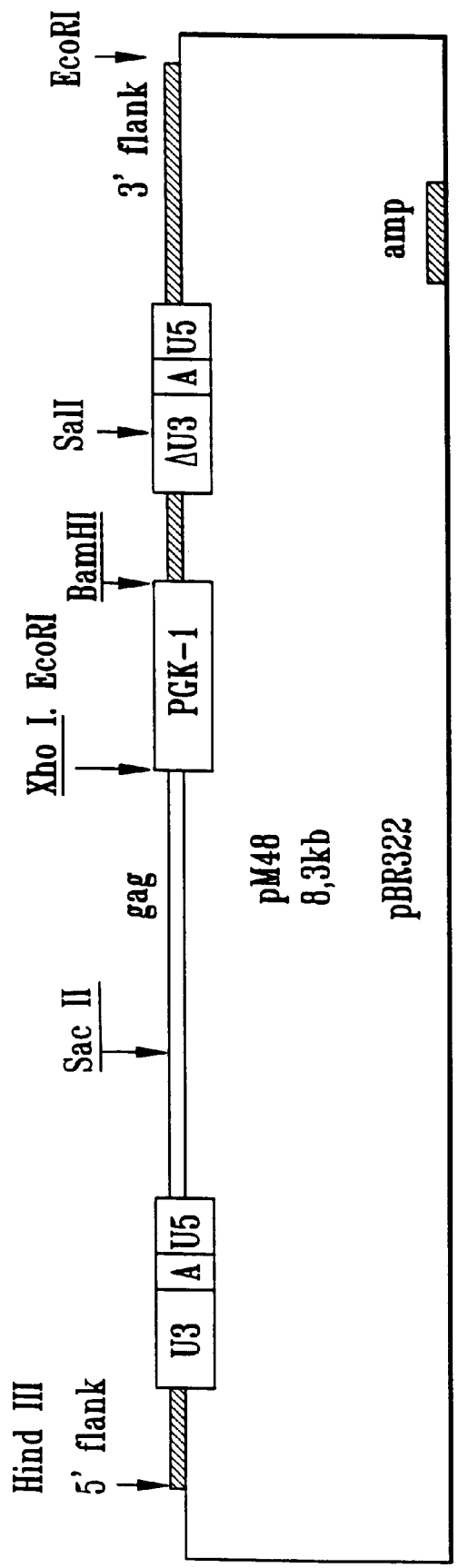
FIG. 2: representation of the vector pM48.

The transfer and expression of exogenous genetic material makes it possible to modify experimentally the properties of the tissue. It has been possible to suggest treatments based on this principle for diseases due to genetic deficiencies or acquired diseases. The example described below makes use of a retroviral vector for introducing into cells the genetic information coding for a secreted protein. The reimplantation in the organism of the genetically modified cells is carried out by combining these cells with collagen, an angiogenic factor and the framework of the coral or cross-linked collagen type. The long-term in vivo expression of the genetic material thus transferred is obtained by using the promoter of the murine phosphoglycerate kinase gene.

1—RETROVIRAL VECTOR 1.1.—Properties

The retroviral vector M48 (FIG. 2) is constructed from proviral sequences isolated from the genomic DNA of rat cells infected with the Moloney murine leukemogenic retrovirus (Mo-MuLV). The gag, pol and env genes which code for the proteins of the virus were deleted and replaced by the sequences to be transmitted. The retroviral sequences in cis necessary for the production and maturation of the transcripts of the recombinant viral genome, for their packaging in infectious viral particles, their reverse transcription and their integration in the genome of the infected cell have been conserved. The sequences of the recombinant provirus and the flanking fragments of cellular DNA are borne by the bacterial plasmid pBR322.

The promoter of the mouse phosphoglycerate kinase (PGK-1) gene was inserted in the place of the viral genes. A unique BamHI cloning site enables the sequences to be transmitted to be placed in the retroviral vector under the control of this promoter.

This retroviral vector bears a deletion in the U3 sequences of the internal LTR (Cone et al., Mol. Cell Biol. 7, 887–897, 1987) This leads to a considerable reduction of the mRNAs being initiated from the 5' LTR and to a predominance of mRNAs produced under the control of the PGK-1 promoter. The use of this vector hence results in the insertion in the genome of the target ell of an expression cassette of the sequence of interest under the control of the PGK-1 promoter.

1.1.—Structure of the Vector

The complete sequence of the vector M48 (FIG. 1) (SEQ ID NO:1) comprises:

Position 1 to 2019: Mo-MuLV sequences comprising the 5' long terminal repeat (or 5' LTR or LTR 5'), the packaging sequences ψ+ which include a part of the gag gene (position −447 to 1564 in the numbering of Shinnick et al. (Nature 293, 543–548, 1981). These sequences are modified as follows: insertion of a SacII linker (5' CCCGCGGG3') at position 1074 (position 626, Shinnick et al.).

This leads to a mutation in phase with the sequence coding for gag.

Position 2020 to 2526: Promoter of the mouse gene coding for phosphoglycerate kinase (position −524 to −20, before the translation start codon, according to Adra et al., Gene 60, 65–74, 1987).

Position 2527 to 2532: Unique BamHI site for the insertion of sequences which will be expressed under the control of the PGK-1 promoter.

Position 2533 to 3101: Mo-MuLV sequences including the 3' end of the env gene (32 codons) and the LTR3'. These sequences are modified as follows: deletion of the U3 sequences of the LTR included between 7935 and 8113 in the numbering of Shinnick et al. and the insertion of a linker SalI (2798 in the present numbering).

Position 3102 to 3674: Rat genomic sequences.

Position 3675 to 8003: Sequences of the plasmid vector pBR322 (position 4363 to 29) comprising the beta-lactamase gene. These sequences are modified as follows: destruction of the BamHI site (position 7657, present numbering).

Position 8004 to 8388: Rat genomic sequences.

1.3.—Production of the Retroviral Vector

This production is carried out by introducing the recombinant proviral structure in a cell line in which the gag, pol and env genes are expressed constitutively.

This line, called a transcomplementary or packaging line, synthesizes retroviral particles lacking genomic RNA. The ψCRIP line derived from NIH/3T3 mouse fibroblasts is used here (Danos and Mulligan, Proc. Natl. Acad. Sci. (USA) 85, 6460–6465, 1988). When the recombinant construction is introduced by transfection, the RNA transcripts from the LTR5' are encapsidated and the cells then produce particles capable of transmitting the recombinant genome but which are incapable of replicating.

After transfection of the recombinant construction the cells producing retroviral vector are selected. Either a clone producing high viral titers or a polyclonal population is used for the preparation of the vector. The steps of isolation of a producing clone are the following:

1) The ψCRIP cells are transfected by a coprecipitate with calcium phosphate (Graham and van der Erb, Virology, 52, 456, 1973) of the retroviral construction and the plasmid pSV2neo (Southern and Berg, J. Mol. Appl. Gen. 1, 327–341, 1982) in a molar ratio of 10 to 1.

2) The cells which have integrated in a stable manner and express the exogenous DNA are selected in the presence of 1 mg/ml G418 (Geneticin, Gibco).

3) The population of cells resistant to G418 in which isolated individual clones are tested for their capacity to produce the retroviral vector. For that purpose, NIH/3T3 target cells are placed in the presence of culture medium recoated from the ψCRIP cells, and the transmission of the recombinant provirus is analyzed after 48 hours. The analysis, performed on the genomic DNA of the target cells, is made by PCR (qualitative method) or by Southern blot (quantitative method).

4) A library of producing cells is stored at −135° C.

2—PREPARATION OF THE STOCKS OF RETROVIRAL VECTOR

The culture supernatant of the packaging cells is recoated after an incubation for 24 hours with the packaging cells producing the retroviral vector and placed in contact with the target cells in order to achieve the infection.

2.1.—Bulk Preparation

A stock of a hundred ampoules containing producing cells is stored at −135° C. After being thawed, the cells are amplified for 10 days, successively in bottles then in roller bottles of 875 cm$^2$, until 20 confluent rollers are obtained. The production is then begun. It lasts 4 or 5 days. The culture medium is DMEM containing 1 g/l of glucose, 10 mM of sodium pyruvate and supplemeted with 5% newborn calf serum (Hyclone). Each roller bottle makes possible the conditioning of 100 ml of medium per 24 hours. This culture supernatant is centrifuged to remove the cell debris. The weekly production is 8 to 10 liters of viral supernatant.

2.2.—Concentration

The supernatant may be concentrated to increase the infectious titer of the retroviral vector. After centrifugation, the supernatant is dialyzed tangentially against a Sartocon membrane of porosity 100,000 by using the Crossflow apparatus of Sartorius. A twenty fold concentration is obtained in 3 hours. It is accompanied by a 20 increase in the infectious titer. After concentration, the viral preparation is used immediately or stored at −80° C. if it is not to be used for at least 2 weeks.

3—SKIN FIBROBLASTS 3.1.—Isolation and Placing in Culture

The fibroblasts intended for the gene transfer are obtained by a cutaneous biopsy performed under very careful aseptic conditions. In the mouse, a syngeneic animal is sacrificed for this purpose. In the large mammal, one or more fragments of skin about 10 cm$^2$ are taken under general anesthesia. After sectioning in strips of several mm$^2$, the fragments are dissociated by an enzymatic treatment. For a fragment of 10 cm$^2$, the reaction is carried out for 2 hours at 37° C. by gentle shaking in 50 ml of RPMI 1640 medium supplemented with 10% fetal calf serum, 100 mg of collagenase (Worthington), 500 U of dispase (Collaborative Research Inc.). After centrifugation and washing the cells are counted then seeded in 150 cm$^2$ bottles at a concentration of 1 to 5×10$^6$/cm$^2$. The culture medium is RPMI 1640 supplemented with 10 to 20% fetal calf serum.

3.2.—Infection by the Retroviral Vector

The infections with the preparation of retroviral vector are started the day after the placing in culture although the cell density is less than 20% of confluence. They are repeated daily following the same protocol for 4 or 5 days. After removal of the culture medium, the cells are placed in contact with the concentrated or unconcentrated retroviral vector preparation, but supplemented in all cases with 8 μg/ml of polybrene. The incubation is carried out for 2 hours at 37° C., then without prior washing the viral preparation is replaced by the culture medium.

When a vector coding for a protein detectable under the microscope is used, it is observed that this process allows the introduction of the foreign gene into more than 90% of the fibroblasts. The level of secretion of the protein into the culture supernatant may be checked during and at the end of this process. All or part of the cells may be frozen at this stage.

After infection, the cells are amplified to produce a number sufficient for reimplantation, i.e. 2–6×10$^8$ cells/kg of body weight. The amplification is carried out on culture trays (multitray, Nunc).

3.3.—Harvesting of the Genetically Modified Cells

After amplification, the cells are harvested by treatment with trypsin. After being washed and counted, they are available to be used for the formation of a neo-organ. A sample is stored to check the genetic transfer by Southern blot as well as the expression and secretion of the foreign protein by a suitable procedure.

EXAMPLE 1

Secretion of a Lysosomal Enzyme (Beta-Glucuronidase) in the Mouse with Implants Containing PTFE Fibers, Rat Tail Collagen and Skin Fibroblasts Modified with a Retroviral Vector

1.1.—Constituents

Three constituents are assembled in vitro. The method described below is applicable to the construction of neo-organs of 1 ml containing $5 \times 10^6$ to $10^7$ genetically modified cells. The same proportions are used for the formation of neo-organs of large size containing 1 to $5 \times 10^9$ cells.

1) Polytetrafluoroethylene fibers (Gore and Associated) sterilized by autoclaving (120° C., 30 minutes) are coated by type 1 collagen. The fibers are bathed in a 0.1% solution of rat tail collagen (Sigma) in 0.1 N acetic acid. This treatment is carried out under vacuum for 1 hour at room temperature in order to expel air present between the synthetic fibers. The collagens of mouse, bovine or human origin may be used indiscriminately. After drying for 24 hours under a hood with laminar air flow, the fibers thus surrounded with a fine film of collagen are incubated in the presence of an angiogenic growth factor (basic FGF, Farmitalia, 10–20 ng/50 mg of fibers in a solution of PBS-5% beta-mercaptoethanol). The fibers thus treated are washed in PBS and stored at 4° C.

2) A solution constituted of the following ingredients is prepared. For 1 ml: 100 µl 10×RPMI 1640 (Gibco); 12 µl 7.5% bicarbonate; 8 µl, 7.5 N NaOH; 2.5 l, 1 M Hepes; 100 µg penicillin/glutamine (Gibco); 10 ng bFGF (Farmitalia); 1.5 mg collagen (Bioethica); distilled water to 1 ml. This solution of syrupy consistency is stored at 4° C.

3) After washing, the genetically modified cells are resuspended in 100 µl of RPMI 1640 with 15% fetal calf serum.

1.2.—Assembly

The in vitro assembly of the neo-organ is carried out under sterile conditions in a hood, in the following manner:

1) 1 mg of treated fibers are spread out in a culture dish (Corning 24 wells plate).
2) The genetically modified cells (100 µl) are incorporated into the collagen solution (1 ml) using a shaker,
3) This mixture is deposited on the fibers.

The entire preparation is placed in an incubator (37° C., 5% $CO_2$) for 30 minutes in order to obtain the gelation of the collagen. When this occurs, 1 ml of RPMI 1640 with fetal calf serum is deposited on the gel in order to compensate the variations in pH. Two to four hours later, the gel is delicately detached from the rim of the culture dish with the aid of an injection needle and transferred to a larger dish in the presence of an excess of culture medium for a period of 12 to 24 hours. During this lapse of time the fibroblasts included in the collagen gel bind to the collagen fibers and this induces a retraction of the structure. It is usual to observe a reduction of more than 50% of the initial volume. The whole is then ready to be implanted in the organism.

1.3.—Implantation

The neo-organ is introduced in the peritoneal cavity in the course of a laparotomy performed under general anesthesia. In the mouse, the implantation is effected by inserting, without binding the neo-organ between the midgut loops in contact with the mesentery. In the large mammal, the neo-organ is fixed by two points between the two layers of the omentum. Vascular connections are established from the first days onwards. The exogenous protein may then be released into the circulation of the recipient animal. As from the third week following the implantation, an organ often pediculate, encapsulated and well individualized is formed. Very many vascular connections are visible at its surface. Inflammatory adhesion does not exist. The examinations at 3 and 6 months show an identical appearance. The histological analysis at this stage reveals the presence of loose, vascularized and only slightly inflamed connective tissue.

1.4.—Treatment of Diseases of Lysosomal Overload

This process was applied to the treatment of a disease of lysosomal overload for which a mouse model is available. It involves a deficit of beta-glucuronidase responsible for a mucopolysaccharidosis. The beta-glucuronidase is phosphorylated and is thus in part transported to the lysosomes and in part secreted in the circulation. It may be picked up by other tissues through the intermediary of the mannose-6-phosphate receptor expressed at the surface of many cell. This specific recovery permits a therapeutic approach in which the continuous systemic distribution of the missing enzyme is ensured by genetically modified cells.

Implants of 0.5 cm$^3$ containing $20 \times 10^6$ autologous fibroblasts are well tolerated by the mouse. The implanted cells express the human beta-glucuronidase gene inserted into the vector M48 under the control of the PGK promoter and secrete the foreign protein for more than 5 months. The biological effect is expressed by a rapid fall in the urinary elimination of the intermediary catabolites of the degradation of the mucopolysaccharides. The histological normalization of the tissues of the recipient animal is spectacular, particularly in the liver and the spleen. It is stable with time and depends on the presence of the neo-organ whose excision induces a return to the initial pathological state.

This process is applicable to the treatment of all of the diseases of lysosomal overload, including Gaucher's disease for which the supply of a soluble form of the glucocerebrosidase can be envisaged.

EXAMPLE 2

Secretion of a Lysosomal Enzyme (Beta-Glucuronidase) in the Dog with Implants Containing PTFE Fibers, Rat Tail Collagen and Skin Fibroblasts Modified with a Retroviral Vector Four dogs received from 1 to 6 neo-organs each containing $10^9$ autologous fibroblasts genetically modified by means of the vector M48-βglu in order to secrete human beta-glucuronidase. Three animals of the Labrador race weighing 21 to 29 kg and one animal of the Beagle race weighing about 9 kg were used. The surgical implantation performed under general anesthesia consisted of inserting the implants between the two parietal and visceral layers of the omentum close to the greater curvature of the stomach. This rapid operation is accompanied by simple operative follow-ups and makes it possible to envisage in the future an implantation by coeliosurgery. One and a half months, four months and six months after the implantation an exploratory laparotomy was performed in order to make a macroscopic check-up of the implant. The identification of the omentum was easy and the detection of the grafted structure was made very quickly. No adhesion was recorded and the vascularization was considerable, including large calibre vessels in connection with the implant. The appearance of the implant has not altered during the period of this observation. A liver biopsy practised at the same time made it possible to investigate the presence of human beta-glucuronidase. The measurement of the activity on cell extracts showed a level equivalent to 2–3% of the endogenous canine activity which was stable with time in the animals having received more than $2 \times 10^9$ genetically modified autologous fibroblasts. The revelation in situ on sections showed an activity localized in the Küpffer cells. The results are summarized in Table I.

TABLE I

Human beta-glucuronidase absorbed by the liver of dogs in which neo-organs were implanted

| | | Number of cells | Activity of human beta-glucuronidase | | | | | | | |
|---|---|---|---|---|---|---|---|---|---|---|
| | | | % endogenous canine activity | | | | In situ revelation on sections | | | |
| Animal | Weight | implanted | day 0 | day 45 | day 120 | day 180 | day 0 | day 45 | day 120 | day 180 |
| Nougatine | 28 kg | $0.8 \times 10^9$ | <0.2 | 3 | 0.8 | — | − | +++ | +/− | − |
| Eglantine | 26 kg | $2 \times 10^9$ | <0.2 | 2 | 2 | 1 | − | +++ | ++ | ++ |
| Doris | 21 kg | $3 \times 10^9$ | <0.2 | 3 | 3 | 1 | − | +++ | +++ | ++ |
| Cydo | 10 kg | $6 \times 10^9$ | <0.2 | nd | 1 | nd | − | nd | nd | nd |

EXAMPLE 3
Secretion of a Lysosomal Enzyme (Beta-L-Iduronidase) in the Mouse with Implants Containing PTFE Fibers, Rat Tail Collagen and Skin Fibroblasts Modified with a Retroviral Vector A cDNA coding for the human beta-L-iduronidase was introduced into the vector M48 and a recombinant retrovirus was produced in the ψCRIP line. Fibroblasts of nude mice were placed in primary culture and infected with this retroviral vector. The cells secreting the human enzyme were introduced into six syngeneic recipients in two neo-organs each containing 10 millions cells.

The animals were sacrificed after 35 to 77 days and the presence of the human enzyme in their liver and spleen was verified by means of a monoclonal antibody. An enzymatic activity equivalent to 1–2% of the endogenous activity was demonstrated, indicating the production of the enzyme from the cells of the neo-organ and its detection at a distance.

EXAMPLE 4
Secretion of Erythropoietin (EPO) in the Mouse with Implants Containing PTFE Fibers, Rat Tail Collagen and Skin Fibroblasts Modified with a Retroviral Vector The nlslacZ gene was excised from the vector M48-nlslacZ by BamHI digestion and replaced by a cDNA coding for mouse EPO synthesized by PCR, thus generating the vector M48EPO. A clone of ψCRE cells producing M48EPO retroviral particles was isolated. A sample of fibroblasts was taken from adult mice by skin biopsy and a primary culture was established in RPMI 1640 medium with 10% FCS. These cells were infected by the vector M48EPO repeatedly for the first 4 days of the culture. Analysis by Southern blot showed that the infected cells contained on average 2 copies of the M48EPO genome per cell. Analysis by Northern blot showed the very predominant expression of the cDNA of the EPO under the control of the PGK-1 promoter. A biological assay of the EPO activity secreted by these cells sa well as an ELISA assay measured a secretion of 17 units of EPO per million cells per 24 hours. These cells were amplified in culture, trypsinized, then resuspended in RPMI 1640 at a concentration of $2.5 \times 10^7$ to $2 \times 10^8$ cells per ml.

Implants were prepared by combining the following ingredients in a 0.9 cm² well: 1) PTFE fibers treated previously as described above to be coated successively with rat tail collagen (Sigma), heparin (Roche) and bFGF (Promega); 2) 1 ml of a solution containing x mg/ml of rat tail collagen (Sigma), bFGF (10 μg/ml) in RPMI 1640 medium; 3) a volume of 10 μl of the suspension of fibroblasts genetically modified to secrete EPO. After having obtained a homogeneous mixture, this latter is solidified by incubation at 37° C. for 30 minutes, then the gel is very carefully separated from the walls of the culture well, transferred to a 35 mm diameter Petri dish coated with RPMI 1640 medium containing 10% FCS and incubated at 37° C. for 3 days. A contraction of the gel occurred during this incubation resulting in a 50% diminution in size. The implants were then inserted in the peritoneal cavity of 14 syngeneic mice with genetically modified fibroblasts.

The weekly measurement of the hematocrit (normal value 46+/−1.5%) showed a progressive rise towards a plateau, the level of which varied as a function of the number of cells secreting EPO in the implants. This plateau was 80% for $2 \times 10^7$ cells, 70% for $10^7$ cells, 60% for $5 \times 10^6$ cells, 52% for $2.5 \times 10^6$ cells. It was maintained at this level during the 6 months period of observation of the animals. The concentrations of EPO in the serum of the mice bearing implants secreting EPO varied from 60 to 400 mU per ml (normal <20 mU/ml).

The implants constituted of PTFE, rat tail collagen and cells genetically modified by the retroviral vector M48EPO thus make possible a stable long-term secretion of EPO in vivo, at high levels estimated to be between 500 and 1500 mU/kg/24 hours, i.e. sufficient in man for the correction of the anemia due to hemoglobinopathies such as sickle cell anemia and beta-thalassemia. Levels 10 fold lower would be sufficient for the treatment of anemia associated with chronic renal insufficiency.

In Vivo Utilization of Implants Containing Coral as Biological Support

1. In the Mouse

In the C3H/He mouse compatibility experiments with Biocoral® as implant showed that it could represent an advantageous alternative to the synthetic supports.

It was in fact possible to coat Biocoral® effectively with different ingredients of the extracellular matrix as well as angiogenic factors. It was shown that murine type I collagen at a concentration of 0.5 mg/ml in 0.001% acetic acid adheres and covers the coral support after drying in air at room temperature for 12 to 24 hours. The presence of this element of the extra-cellular matrix then made possible the irreversible binding of the basic fibroblast growth factor labelled with $^{125}I$ ($^{125}I$-basic Fibroblast Growth Factor) (bFGF) to Biocoral®. In this was the binding of an average of 50 ng of bFGF to 40 mg of coral support pretreated with murine type I collagen was achieved. Although this binding could have also been done in the absence of pretreatment with collagen, in this latter case it was reversible, hence of low affinity. Collagen is thus an essential intermediary and justified for the stable binding of angiogenic factors to Biocoral. Finally, it was possible to increase the binding of bFGF five to ten fold when the coating of 40 mg of Biocoral by collagen was supplemented by 200 μg heparan sulfate (Sigma) (1 mg/ml solution in PBS) or 500 units of heparin (Roche) (5000 units/ml solution). These two components of the extracellular matrix have a known affinity for collagen (Baird, A., Schubert, D., Ling, N. and Guillemin, R (1988) Receptor and heparin binding domains of basic fibroblast growth factor. Proc. Natl. Acad. Sci. USA 85, 2324–2328). Their anionic and polysulfated properties are responsible for the strong affinity for the bFGF (Johnson, D. E., Lee, P. L., Lu, J., and Williams, L. T. (1990) Diverse forms of a receptor for acidic and basic fibroblast growth factors. Mol. Cell. Biol. 10, 4728–4739). After incubation in the presence of one or other of these components 1 h at 4° C. with shaking, the Biocoral was dried in air at room temperature. Thus heparinized, the coral has an anti-coagulant action.

Assays of subcutaneous implantation with 40 mg of high porosity (50%) spherical coral coated with murine type I collagen and bFGF (=50 ng/40 mg of coral) were performed in vivo on ten mice. The macroscopic and histological appearance of these implants was analyzed over a period of 7 months. The results show that Biocoral was progressively resorbed during several months and was replaced by a structure formed of vascularized connective tissue having the initial spherical form of the coral implant with, however, a reduction in volume of approximately a third. The histological analysis of this connective tissue at three months showed an intense vascularization and the total absence of inflammatory cells in spite of the corral residues present. The actual connective tissue was formed of only slightly dense mesenchymal cells, surrounded by newly formed collagen fibers. The analysis at 7 months showed similar results without involution.

2. In the Dog

In the 25 kg dog we carried out a first implantation experiment with a neo-organ, the external part of which made of porous coral (50%) made it possible to retain a retracted collagen gel containing 1 to 2×10⁹ genetically modified autologous fibroblasts. The Biocoral support had been coated with murine type I collagen and heparin (Roche). After drying, the coral thus pretreated was incubated in the presence of an angiogenic growth factor of the bFGF type (Farmitalia) then rinced with PBS. The surgical implantation performed under general anesthesia consisted of inserting the whole implant between the two parietal and visceral layers of the omentum close to the greater curvature of the stomach. This rapid operation made possible simple operative follow-ups and makes it possible to envisage in the future and implantation by coeliosurgery. Forty five days after, an exploratory laparotomy was performed in order to make a macroscopic check-up of the implant. The identification of the omentum was easy, no adhesion was noted and the detection of the coral implant, containing the genetically modified autologous fibroblasts, was made very quickly. It was not possible to observe any adhesion and the vascularization was considerable, including large calibre vessels in connection with the implant. A process of progressive resorption of the coral was observed for at least 4 months.

3. Other Mammals

The creation of new-organs by using Biocoral suited to surgical implantation in large mammals, in particular man, with a view to their clinical development is carried out analogously. Biocoral can be modulated in its design, is capable of triggering a sustained angiogenesis combined with its own resorption and, finally, is devoid of inflammatory local and systemic effects. Such a biomaterial advantageously serves as receptacle and skeleton for a type I collagen gel containing genetically modified autologous cells, capable of secreting a therapeutic factor in the circulation once the vascular connections are established.

EXAMPLE 5

Secretion of Erythropoietin (EPO) in the Mouse with Implants Containing Fragments of Coral, Rat Tail Collagen and Skin Fibroblasts Modified with a Retroviral Vector In the same manner as in Example 4, mouse fibroblasts were obtained from a skin biopsy, placed in culture and transduced with the vector M48EPO. After amplification, the cells were trypsinized and resuspended in RPMI 1640 medium containing 10% FCS at a concentration of $10^8$ cells per ml.

Implants were prepared by combining the following ingredients in a 0.9 cm² well: 1) coral powder (Inoteb) composed of particles of porosity >45% and a granulometry between 600 and 1000 μm, the pores of which had a mean diameter of 150 μm, previously treated by incubation in a solution of rat tail collagen (1 mg/ml) for 30 minutes at room temperature, dried, then incubated in a heparin solution (Roche) for 30 minutes at room temperature, dried, then incubated in a 100 μg/ml solution of bFGF (Promega) for 30 minutes at room temperature; 2) 1 ml of a solution containing 3 mg/ml of rat tail collagen (Sigma), bFGF (100 μg/ml) in RPMI 1640 medium; 3) a volume of 100 μl of the suspension of fibroblasts genetically modified to secrete EPO. As in the examples 1 to 3, a homogeneous mixture of these constituents was solidified by incubation at 37° C. for 30 minutes, then the gel was very carefully separated from the walls of the culture wells, transferred to a 35 mm diameter Petri dish, coated with RPMI 1640 medium containing 10% FCS and incubated at 37° C. for 3 days. The implants were then inserted in the peritoneal cavity of 3 syngeneic mice with genetically modified fibroblasts.

As in Example 4, the measurement of the hematocrit of the animal recipients showed a rapid increase reaching a plateau after 3 weeks, and which was maintained at this level for all of the period of the observation (2 months). Implants formed of a structured collagen gel with fragments of coral thus make possible the maintenance in the functional state of genetically modified fibroblasts implanted in the peritoneal cavity of recipient animals, as well as the long-term secretion of a soluble protein in the serum.

EXAMPLE 6

Secretion of Erythropoietin (EPO) in the Mouse with Implants Containing Cross-Linked Collagen Fibers, Rat Tail Collagen and Skin Fibroblasts Modified with a Retroviral Vector A similar experiment to the Examples 4 and 5 consisted of producing implants combining mouse fibroblasts transduced with the M48EPO vector, rat tail collagen and a support formed of cross-linked collagen fibers (Imedex). The preparation was made in the following manner: 1) the fibers dehydrated and sterilized by radiation were first rehydrated by incubation for 12 hours at 4° C. in RPMI 1640 medium. They were then incubated at room temperature for 30 minutes in RPMI 1640 containing 10% FCS and 100 μg/ml of bFGF (Promega), then loaded into a 0.4 cm² well to which was added 1 ml of RPMI 1640 solution containing FCS (10%), rat tail collagen (1 mg/ml), bFGF (100 μg/ml, Promega) and $10^7$ fibroblasts genetically modified to secret EPO. After solidification at 37° C. for 30 minutes, the gel was then very carefully detached from the walls of the culture well, transferred to a 35 mm diameter Petri dish and coated with RPMI 1640 medium containing 10% FCS. The implants were incubated for 3 days at 37° C., moderate contraction of the structure was observed, then they were implanted in 3 syngeneic mice.

In a manner similar to that described in the Examples 4 and 5, the weekly measurement of the hematocrit showed a progressive rise until a plateau was reached which was maintained for the duration of the observation period (2 months). Implants formed of a structured collagen gel with cross-linked collagen fibers thus make possible the maintenance of the functional state of genetically modified fibroblasts implanted in the peritoneal cavity of animal recipients as well as the long-term secretion of a soluble protein in the serum.

EXAMPLE 7
Detoxification of Bilirubin by Glucurono-Conjugation in Rats Bearing Implants Containing PTFE Fibers, Rat Tail Collagen and Genetically Modified Fibroblasts Expressing the Enzyme UDP-Glucuronosyl Transferase Bilirubin is a degradation product of the haem produced continuously and in considerable quantity by the organism. Bilirubin is liposoluble and can penetrate passively into cells where its accumulation is toxic. The elimination of bilirubin is achieved by glucurono-conjugation in the hepatocyes by the enzyme bilirubin UDP-glucuronosyl transferase (bil. UDPGT) which exists in two known isoforms (1 and 2). The addition of glucuronic acid makes the molecule water soluble, non-toxic and makes possible its excretion in the bile. Complete hereditary deficit of bil. UDPGT activity is responsible for a very serious disease (Crigler-Najjar disease) which requires liver transplantation. There exits a model for this disease in the rat (Gunn rat).

The rat cDNA coding for the isoform 2 (bil.UDPGT-2) and human cDNA coding for isoform 1 (bil.UDPGT-1) were inserted into the M48 vector after excision of the nislacZ gene by the BamHI enzyme, thus generating the vectors M48GT-2 and M48GT-1. In a manner similar to that described in Examples 1, 3 and 4 samples of Gunn rat fibroblasts were taken by skin biopsy, placed in culture and transduced by the vector M48GT-2. The presence of, on average, one copy of the vector genome in the transduced cells was verified by Southern blot, and the expression under the control of the PGK promoter was verified by Northern blot. The bil.UDPGT enzymatic activity was detected in the microsomal extracts of the infected fibroblasts. The cells were amplified in culture, trypsinized then resuspended in RPMI 1640 at a concentration of $2\times10^8$ cells per ml.

Implants containing $2\times10^7$ genetically modified cells were prepared in the same manner as in Examples 1, 3 and 4. Two implants were inserted in the peritoneal cavity of each recipient Gunn rat. As the colony of Gunn rats used is not inbred, care was taken that each animal is reimplanted with its own cells. The measurement of the unconjugated bilirubin concentrations in the treated animals and in control rats of the same age showed a significant and stable diminution (between 20 and 50%) during a period of observation of 2 months in rats bearing implants of fibroblasts expressing the bil.UDPGT. Bile samples were collected when the animals were sacrificed and analyzed by high pressure liquid chromatography (HPLC). Whereas the untreated animals show a total absence of conjugated bilirubin in the bile, the Gunn rats bearing implants containing fibroblasts expressing the bil.UDPGT showed peaks identified as mono- and di-conjugated bilirubin. The proportion of conjugated bilirubin attained up to 11% of the bilirubin present in the bile.

These results indicate that rat fibroblasts transduced with the vector M48UDPGT-1 and grafted into Gunn rats in the form of implants combining PTFE fibers and rat tail collagen are capable of achieving in vivo the glucurono-conjugation reaction of bilirubin, and the conjugated bilirubin can then be eliminated in the bile by the hepatocytes, thus making possible a partial correction of the phenotype of the diseased animals. It is thus possible to achieve the detoxification of biological products in vivo by means of genetically modified fibroblasts implanted in a structured collagen gel with PTFE fibers.

EXAMPLE 8
Use of an Inducible Promoter (Mx) to Modulate the Expression of a cDNA Inserted in a Retroviral Vector In the case of implants secreting a protein continuously into the circulation, it would be desirable to be able to exercise control over this secretion. In order to do this a retroviral vector derived from the vector M48 was constructed in which the PGK-1 promoter was excised and replaced by a fragment of 250 bp covering the region −250 to +1 of the promoter of the Mx gene of the mouse. This promoter comprises elements of reponse to stimulation by alpha and beta interferons. In the mouse the protein Mx is expressed in response to a secretion of alpha or beta interferon. In a manner similar to that in Examples 3, 4 and 5, the cDNA coding for mouse EPO was inserted into this vector at the BamHI site, thus generating the vector MxEPO. ψCRE cells producing recombinant ecotropic retroviral particles containing the genome of the vector MxEPO were isolated. Fibroblasts isolated from a skin biopsy performed on a mouse were infected with the vector MxEPO, and the EPO secreted into the supernatant of these cultures was measured before and after addition of alpha interferon (1000 units per ml) in the culture medium. The basic secretion levels of EPO were less than 0.3 units/ml/24 hours, evidence for a low activity of the Mx promoter present in the MxEPO vector in the absence of interferon. An increase in the secretion up to 10 fold the basic level was measured after addition of alpha interferon. This high secretion is maintained for at least 6 days. This observation shows that a control may be exercised over a transcriptional promoter inserted into a retroviral vector after the integration of the latter in the genome of the target cell.

Implants constituted of PTFE fibers, rat tail collagen and containing skin fibroblasts transduced with the MxEPO vector were prepared and implanted in syngeneic mice. In the absence of other treatment, these animal have maintained a normal hematocrit. Some of the recipient animals were treated by the intra-peritoneal injection of 50 mg of polyA-U (Boehringer) each 48 hours for two weeks in order to raise the hematocrit.

Treatment of Genetic or Acquired Diseases

The process if applicable to the delivery to the serum of any soluble protein or transmembrane proteins lacking their membrane immobilization domain. However, it does not permit regulation of the serum concentrations of the foreign protein. The following applications are envisaged for genetic diseases: in hemophilia B, the supply of factor IX; in hemophilia A, the supply of factor VIII in the form of a protein deleted in the B region; in beta-thalassemia, the supply of erythropoietin capable of correcting the anemia by stimulation of fetal hemoglobin synthesis.

The supply of soluble CD4 or its derivatives coupled to immunotoxins and immunoglobulins is conceivable in infections by retroviruses of the HIV family. More generally, any soluble anti-viral protein could be delivered in this manner.

Production of Antibodies

The circulation of a foreign protein in the mouse induces an immune response marked by the appearance of specific antibodies as we have observed for beta-glucuronidase, the soluble CD4 and erythropoietin. The process could thus be applied to immunise animals against the still unidentified product of a cDNA isolated by reverse genetics or by other means. It should be possible to obtain polyclonal or monoclonal antibodies in this manner without necessitating the prior preparation of the protein.

The same approach can be envisaged to achieve immunizations for a therapeutic or prophylactic purpose. It should be possible to suggest vaccinating preparations, for example, against neutralizing epitopes of the envelope of HIV or related viruses.

Regulation by the Tet Operator/Tet Repressor System

Skin fibroblasts are prepared in which two retroviral vectors are introduced, one coding for the protein of interest placed under the control of a promoter comprising the tet operator elements, the other coding for the tet repressor or a related molecule modified in order to produce an enhancer effect. Depending on the nature of this latter element and that of the promoter containing the operator sequences, the addition of tetracycline will induce an enhancement or a repression of transcription. The fibroblasts transduced with these two vectors are implanted in vivo in a neo-organ and the animals are treated with tetracycline in order to assess the induction of expression. The reporter gene is preferably that of the mouse EPO.

Regulation by the Progesterone Receptor Modified in Order to Induce Transcription in the Presence of RU486

When its C-terminal region is cleaved the progesterone receptor becomes capable of stimulating transcription in the presence of RU486. Skin fibroblasts are infected with two retroviral vectors, one coding for the protein of interest expressed under the control of a promoter comprising elements of reponse to progesterone, the other coding for a truncated version of the progesterone receptor. As previously, the fibroblasts transduced by these two vectors are implanted in neo-organs in the mouse and the animals are treated with RU486.

We claim:

1. An implant comprising:
   (a) a biocompatible support permitting the biological anchoring of cells, wherein said biocompatible support comprises high porosity coral;
   (b) cells transduced by a nucleotide sequence encoding a defined polypeptide and having the capacity to express said polypeptide; and
   (c) a constituent capable of inducing and/or promoting the gelation of said cells.

2. The implant according to claim 1, wherein said biocompatible support is at least partially resorbable in vivo.

3. The implant according to claim 1, wherein said high-porosity coral biocompatible support has a spherical shape.

4. The implant according to claim 1, wherein said constituent capable of inducing and/or promoting the gelation of the cells is collagen.

5. The implant according to claim 1, wherein said constituent capable of inducing and/or promoting the gelation of the cells is selected from supports based on:
uncross-linked collagen, or
alginates.

6. The implant according to claim 1, wherein said cells have the capacity to be tolerated immunologically by an organism to which they are administered, and have been transduced by a nucleotide sequence coding for a defined polypeptide.

7. The implant according to claim 6, wherein said transduced cells are fibroblasts.

8. The implant according to claim 1, wherein said transduced cells comprise a retroviral vector comprising a proviral DNA sequence in which:
the gag, pol and env genes of the proviral DNA have been deleted at least in part in order to produce a proviral DNA incapable of replicating this DNA being in addition incapable of recombining to form a wild-type virus,
the LTR sequence contains a deletion in the sequence U3 such that transcription of the mRNA that it controls is reduced, and the retroviral vector comprises, in addition, an exogenous nucleotide sequence under the control of a promoter.

9. The implant according to claim 8, wherein said proviral DNA of the vector is derived from the MuLV retrovirus.

10. The implant according to claim 8, wherein said sequences of the pol and env genes of the proviral DNA are entirely deleted.

11. The implant according to claim 8, wherein the U3 region of the LTR3' fragment of the proviral DNA is deleted at nucleotide 2797 of SEQ ID NO:1.

12. The implant according to claim 8, wherein said exogenous nucleotide sequence is under the control of the mouse PGK-1 promoter or the human PGK-1 promoter, optionally lacking a "TATA box".

13. The implant according to claim 8, wherein said proviral sequence upstream from a promoter of the exogenous nucleotide sequence is the proviral nucleotide sequence situated between nucleotides 1 and about 1500 of SEQ ID NO:1.

14. The implant according to claim 8, wherein said retroviral vector is the vector pM48 shown in FIG. 2, comprising the exogenous nucleotide sequence at the BamHI site.

15. The implant according to claim 1, wherein said cells are tumor cells transduced with an exogenous nucleotide sequence.

16. The implant according to claim 1, wherein said cells are transduced with a vector containing one or more exogenous nucleotide sequences coding for an antigen or an antigenic determinant or coding for a polypeptide or glycoprotein soluble in the serum.

17. The implant according to claim 1, further comprising one or more angiogenic factor.

18. The implant according to claim 1, further comprising heparin or a heparin derivative.

19. The implant according to claim 1, comprising from $10^6$ to $10^9$ transduced cells.

20. A method of temporary or permanent delivery of a desired polypeptide to a human or animal comprising implanting into the human or animal an implant according to claim 1.

21. A method for administering cells to a human or animal comprising implanting into the human or animal an implant according to claim 1:
either for the treatment of genetic diseases, wherein an exogenous nucleotide sequence contained in the cells code for beta-glucuronidase, for the factor VIII, factor IX or erythropoietin;
or for the treatment of acquired diseases;
or for the treatment of tumors, wherein the exogenous nucleotide sequence contained in the transduced cells code for a substance capable of promoting or enhancing the immune response against the cells of the tumors.

22. A composition comprising an implant according to claim 1 with one or more substances.

23. A method of treatment of genetic diseases, acquired diseases or tumors, said method comprising the introduction into man or animals of an implant according to claim 1 for a period of time sufficiently long to allow the cells included in said implant to produce in vivo a peptide, a protein or a glycoprotein having a therapeutic effect on the disease to be treated.

24. A method according to claim 23, wherein said implant is introduced in the peritoneal cavity, the peri-renal space or the skin of the patient to be treated.

25. A method of preparation of an implant according to claim 1, said method comprising the steps of:
placing of the biocompatible support in contact with said cells and a constituent capable of inducing and/or promoting their gelation;
incubation of the preparation obtained in the previous step in order to obtain the gelation of said constituents;
culture of the cells thus obtained under conditions allowing them to bind to the gelled constituents and
recovery of the implant thus obtained.

26. The method according to claim 25, wherein said biocompatible support is placed in contact with cells previously incorporated into a solution of collagen.

27. The method according to claim 25, wherein said biocompatible support is constituted of coral powder, previously treated with a solution of collagen or a growth factor.

28. A kit for the preparation of an implant to achieve the in vivo expression and secretion by cells of a substance to produce a desired therapeutic effect, said kit containing:
a biocompatible support comprising high porosity coral making possible the biological anchoring of said cells; and
a constituent capable of inducing and/or promoting the gelation of said cells.

29. The kit according to claim 28, wherein said constituent capable of inducing and/or promoting the gelation of the cells is collagen.

30. The kit according to claim 28 comprising a DNA comprising a sequence coding for the substance expressed and secreted by said cells.

31. A kit for the preparation of an implant to achieve the in vivo expression and secretion by cells of a substance to produce a desired therapeutic effect, said kit containing:
a biocompatible support comprising high porosity coral making possible the biological anchoring of said cells;
a constituent capable of inducing and/or promoting the gelation of said cells; and the retroviral vector according to claim 8.

32. The kit according to claim 28, comprising cells having the capacity to express and secrete naturally or after recombination a defined substance.

33. A kit for the preparation of an implant to achieve the in vivo expression and secretion by cells of a substance to produce a desired therapeutic effect, said kit containing:

a biocompatible support comprising high porosity coral making possible the biological anchoring of said cells; and a constituent capable of inducing and/or promoting the gelation of said cells wherein said cells are transduced cells having the capacity to be tolerated immunologically by the organism to which they are administered, and wherein said cells comprise a retroviral vector according to claim 8.

34. An implant comprising:
(a) a biocompatible support permitting the biological anchoring of cells, wherein said support consists of high-porosity coral,
(b) fibroblast cells transduced by a nucleotide sequence encoding a polypeptide and having the capacity to express and secrete said polypeptide; and
(c) a constituent capable of inducing and/or promoting the gelation of said cells, wherein said constituent is collagen.

35. An implant comprising:
(a) a biocompatible support permitting the biological anchoring of cells, wherein said support consists of high-porosity coral,
(b) cells transduced by a retroviral vector comprising a nucleotide sequence encoding a polypeptide and having the capacity to express and secrete said polypeptide; and
(c) a constituent capable of inducing and/or promoting the gelation of said cells, wherein said constituent is collagen.

* * * * *